(12) United States Patent
Jarrell et al.

(10) Patent No.: US 8,317,518 B2
(45) Date of Patent: Nov. 27, 2012

(54) TECHNIQUES FOR IMPLEMENTING VIRTUAL PERSONS IN A SYSTEM TO TRAIN MEDICAL PERSONNEL

(75) Inventors: Bruce Jarrell, Severna Park, MD (US); Sergei Nirenburg, Reisterstown, MD (US); Marjorie Joan McShane, Reisterstown, MD (US); Stephen Beale, Bel Air, MD (US)

(73) Assignees: University of Maryland, Baltimore, Baltimore, MD (US); University of Maryland, Baltimore County, Baltimore, MD (US)

( * ) Notice: Subject to any disclaimer, the term of this patent is extended or adjusted under 35 U.S.C. 154(b) by 1148 days.

(21) Appl. No.: 11/672,161

(22) Filed: Feb. 7, 2007

(65) Prior Publication Data

US 2008/0015418 A1 Jan. 17, 2008

Related U.S. Application Data

(63) Continuation-in-part of application No. 11/045,657, filed on Jan. 28, 2005.

(60) Provisional application No. 60/771,316, filed on Feb. 8, 2006.

(51) Int. Cl.
*G09B 23/28* (2006.01)

(52) U.S. Cl. .......... 434/262; 434/267; 434/272

(58) Field of Classification Search .......... 434/262, 434/267, 272; 703/6, 11
See application file for complete search history.

(56) References Cited

U.S. PATENT DOCUMENTS

| | | | | |
|---|---|---|---|---|
| 5,385,474 A | * | 1/1995 | Brindle | 434/267 |
| 6,126,450 A | * | 10/2000 | Mukai et al. | 434/262 |
| 6,692,258 B1 | * | 2/2004 | Kurzweil et al. | 434/262 |
| 6,850,944 B1 | * | 2/2005 | MacCall et al. | 1/1 |
| 7,024,399 B2 | * | 4/2006 | Sumner et al. | 706/45 |
| 7,107,253 B1 | * | 9/2006 | Sumner et al. | 706/45 |
| 7,510,398 B1 | * | 3/2009 | Thornton | 434/262 |
| 7,653,556 B2 | * | 1/2010 | Rovinelli et al. | 705/2 |
| 2004/0086873 A1 | * | 5/2004 | Johnson et al. | 435/6 |
| 2004/0153435 A1 | * | 8/2004 | Gudbjartsson et al. | 707/1 |
| 2005/0131649 A1 | * | 6/2005 | Larsen et al. | 702/19 |
| 2005/0170323 A1 | * | 8/2005 | Jarrell et al. | 434/262 |
| 2005/0267721 A1 | * | 12/2005 | Thalhammer-reyero | 703/11 |

(Continued)

OTHER PUBLICATIONS

J.A. Gordon, et al., Bringing good teaching cases "to life": a simulator-based medical education service, Academic Medicine, Jan. 2004, pp. 23-27, vol. 79, No. 1.

(Continued)

*Primary Examiner* — Xuan Thai
*Assistant Examiner* — Bruk Gebremichael
(74) *Attorney, Agent, or Firm* — Evans & Molinelli PLLC; Eugene J. Molinelli

(57) ABSTRACT

Techniques for delivering medical care include receiving normal data that indicates normal conditions in a patient. Abnormality data is received and indicates an abnormal condition, if any, in a patient. An instance of a virtual patient is generated based on the normal data and the abnormality data. The instance includes a physiological component that describes a sufficiently comprehensive physical state of a patient having the abnormal condition to simulate clinical measurements of the patient's condition. The instance also includes a cognitive component that describes a patient's awareness of symptoms, history of behavior and ability to convey information in response to queries. Action data is received from a trainee. Response data is generated based on the action data and the instance. Display data is presented based on the response data, and indicates information about the instance available as a result of the requested action.

19 Claims, 11 Drawing Sheets

U.S. PATENT DOCUMENTS

2006/0004609 A1* 1/2006 Kenneth et al. .................... 705/3
2006/0040245 A1* 2/2006 Airola et al. ................... 434/262
2007/0094188 A1* 4/2007 Pandya et al. ................... 706/45

OTHER PUBLICATIONS

S.P. Lajoie, et al, Tutoring strategies for effective instruction in internal medicine, International Journal of Artificial Intelligence, , pp. 293-309, vol. 12.

N.F. Noy, et al., Pushing the envelope: challenges in a frame-based representation of human anatomy, Data and Knowledge Engineering, 2004, pp. 335-339, vol. 48.

Susan M. Williams, Putting case-based instruction into context: Examples from legal and medical education, The Hournal of the Learning Sciences, 1992, pp. 367-347, vol. 2, No. 4, Publisher: Lawrence Eribaum Associates, Inc., Published in: US.

United States Office Action for corresponding U.S. Appl. No. 11/045,657, dated Jun. 24, 2010, pp. 1-20 US.

* cited by examiner

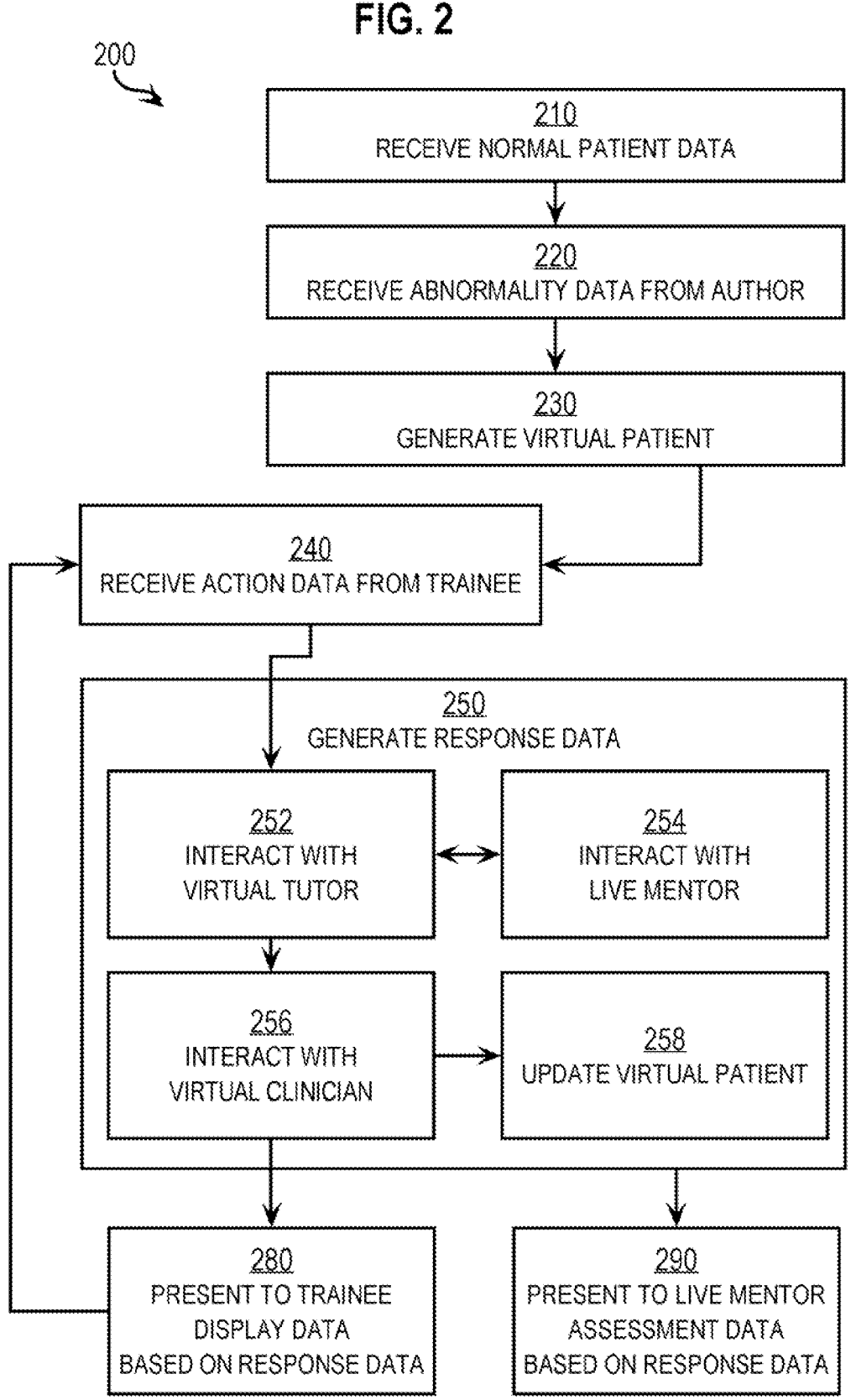

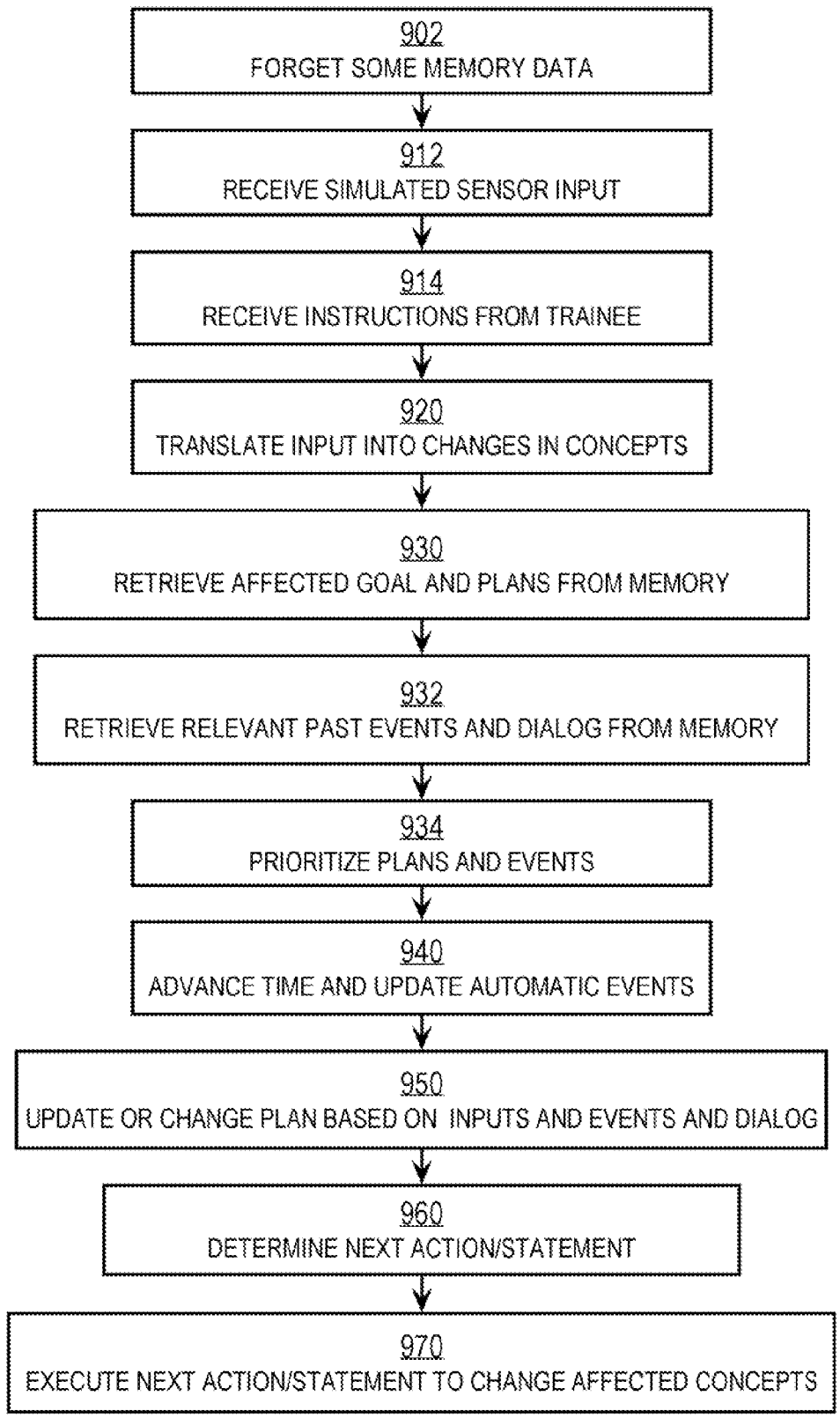

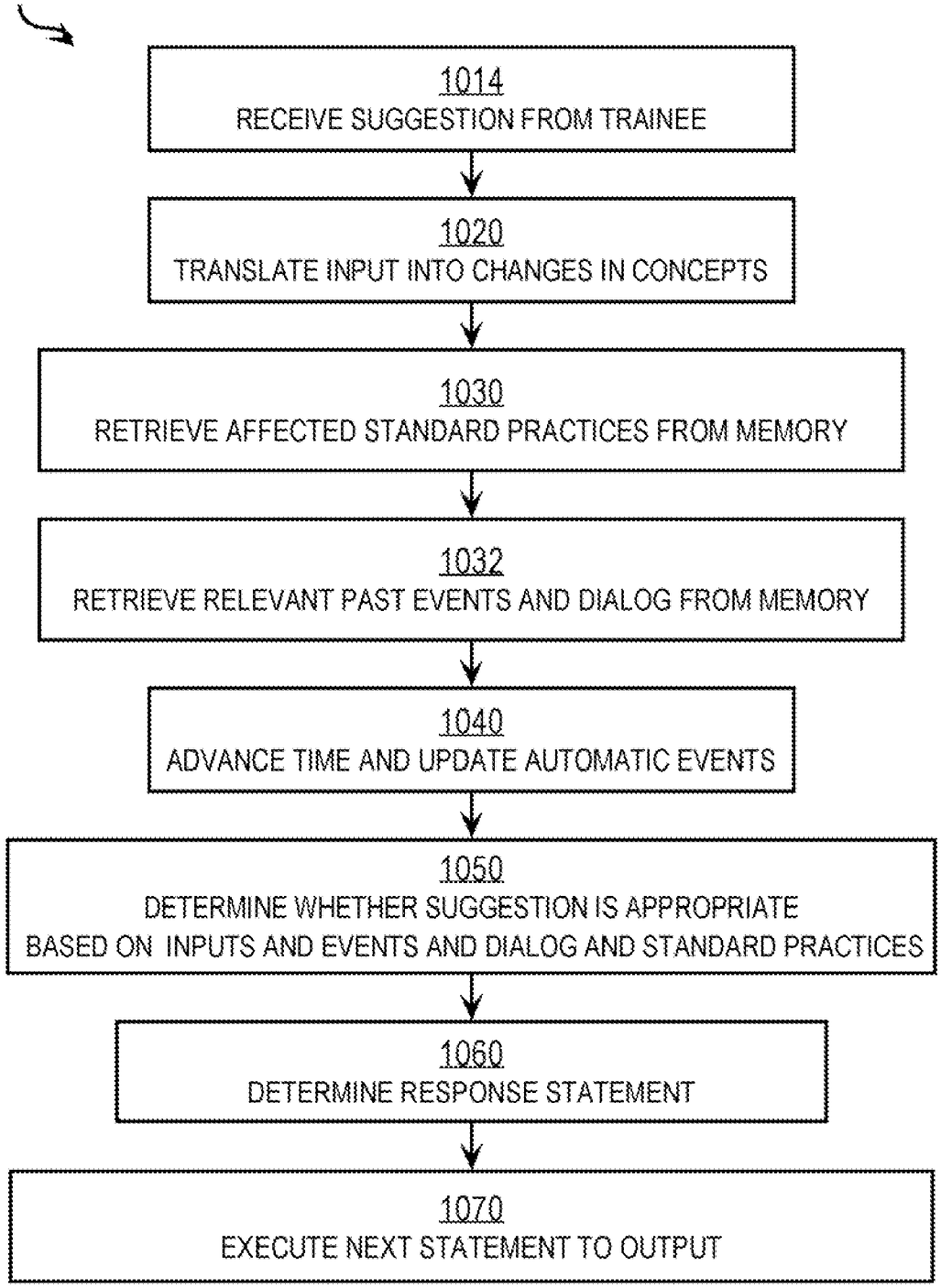

TECHNIQUES FOR IMPLEMENTING VIRTUAL PERSONS IN A SYSTEM TO TRAIN MEDICAL PERSONNEL

CROSS-REFERENCE TO RELATED APPLICATIONS

This application claims benefit as a Continuation-in-part of application Ser. No. 11/045,657, filed Jan. 28, 2005, under 35 U.S.C. §120.

This application also claims benefit of Provisional Appln. 60/771,316, filed Feb. 8, 2006, the entire contents of which are hereby incorporated by reference as if fully set forth herein, under 35 U.S.C. §119(e).

STATEMENT OF GOVERNMENTAL INTEREST

This invention was made in part with Government support under Contract No. DAMD17-03-2-0001 awarded by the Department of the Army. The Government has certain rights in the invention.

BACKGROUND OF THE INVENTION

1. Field of the Invention

The present invention relates to medical care delivery, and in particular to improving medical care delivery by improving decision-making skills of medical personnel with systems that simulate interactions with a mentor or a patient using a virtual patient or virtual tutor or both.

2. Description of the Related Art

Medical care delivery is major industry in the United States. An important component of medical care delivery is a cadre of trained medical care professionals who can diagnose patient condition and prescribe treatment protocols using cognitive skills. The fewer errors made by this cadre, the better is the medical care delivered. Currently, cognitive skills of medical care professionals are developed by close interaction with other members of the profession who are already highly skilled and serve as mentors. Of those already skilled only some are good mentors. The more people trained by the good mentors, the better the medical care delivered.

Individuals who are both good physicians and good mentors have limited time, energy and patience to effectively train all medical care profession students and professionals undergoing continuing medical education, collectively called herein medical trainees. To compound the problem, trainees have a limited time to train. Both mentors and trainees would greatly benefit from an automated system that takes on some or most of this burden.

Recently, medical trainees have had their workweek limited to 80 hours. Under this constraint, they must safely complete their required patient care duties while still fulfilling the requirements of a rigorous educational program. In addition, the content of this educational program must evolve continuously by being updated and re-prioritized given the remarkable progress in areas such as the human genome project and molecular biology. Physicians are expected to remain broadly knowledgeable and specifically expert, yet there are no good automated methods to support accomplishing these expectations. Currently, physicians learn information through reading, conferences, one-on-one discussions with experts who are effective mentors, and trial-and-error management of real patients. Safer and more efficient methods for becoming expert and reducing error rates prior to patient contact are desirable.

A number of expert systems have been developed to capture the expertise of medical professionals. Some of these expert systems have been used in the training of students preparing for the medical profession. Training strategies emanate from the work of Ericsson, K. A. (Ed.) (1996). *The Road to Excellence: The Acquisition of Expert Performance in the Arts and Sciences, Sports and Games.* Mahwah, N.J., Lawrence: Lawrence Erlbaum Associates. These strategies indicate that the acquisition of expertise in skills and cognitive knowledge is, among other factors, strongly related to deliberate sessions to rehearse well-defined tasks and to obtain immediate feedback designed around ways to improve performance. These strategies have been applied to technical skills training in medicine through the simulation of manual procedures, such as insertion of a chest tube, in part-task trainers. Progress in this area has been slow due to the complex nature of the simulation. Application of these strategies to cognitive skills has been even more difficult, as evidenced by the extensive work done and few resultant successes for expert systems, intelligent tutors and similar systems.

While prior approaches serve as suitable aids for some procedures and isolated organ systems, these expert systems suffer some deficiencies. For example, accepted practice dictates one or a few certain sequences of steps to isolate and treat a problem, and expert systems capture this standard practice. Existing training systems, to varying degrees, capture one or more standard practices and reward a trainee who follows them. Little feedback is provided to a student who deviates from accepted practice, other than to stop the process and report a failure.

However, patient care is a complex problem and procedures change as new understanding and new technology become available. Therefore teaching medical trainees to follow accepted practice by rote is not good training for understanding how the standard practice evolved and is likely to evolve into the future. Furthermore, a patient with multiple conditions may involve different practices that may be confusing to implement together, or, even worse, incompatible for combination. For understanding sufficient to function at such levels, it is preferable to teach trainees to address patient care as discovering the most effective treatment for a complex problem using a variety of knowledge sources, information gathering procedures, incremental logic, treatments and interventions—a cognitive process used by the most successful practitioners and successfully taught by the more successful mentors. In some cases, a successful mentor stops the trainee who is deviating too far, in some cases a successful mentor suggests alternatives to consider, and in some rare cases that do not endanger a patient, the mentor may let the trainee arrive at the accepted response through a circuitous route of self discovery.

Based on the foregoing, and other aspects of the problem described in more detail below, there is a clear need for automated systems that take on some or most of the burden of conveying cognitive skills to medical trainees.

SUMMARY OF THE INVENTION

Techniques are provided for delivering medical care by improving decision-making skills to medical personnel who deliver the care.

In a first set of embodiments, a method includes receiving normal data that indicates normal conditions in a patient. Abnormality data is received and indicates an abnormal condition, if any, in a patient. An instance of a virtual patient is generated based on the normal data and the abnormality data. The instance includes a physiological component that describes a sufficiently comprehensive physical state of a patient having the abnormal condition to simulate clinical measurements of the patient's condition. The instance also includes a cognitive component that describes a patient's awareness of symptoms, history of behavior and ability to convey information in response to queries. Action data is received from a trainee. Response data is generated based on the action data and the instance. Display data is presented based on the response data, and indicates information about the instance available as a result of the requested action.

In some of these embodiments, medical information is stored and processed using constructs of a natural language processor.

In some embodiments of the first set, the cognitive component includes history data that indicates a previous value for a particular object and a previous occurrence of a phase in a particular event. The response is generated based on the history data.

In some embodiments of the first set, the cognitive component includes goal data and plan data. The goal data indicates a goal for the virtual patient; and the plan data indicates one or more plans for achieving the goal. Generating response data includes determining a next step in a particular plan indicated in the plan data and executing the next step in the particular plan.

In some embodiments of the first set, the cognitive component includes language data that indicates an ability of the virtual patient to understand and express concepts in a particular language. Generating response data includes generating response data based on the language data.

In some embodiments of the first set, the method includes receiving tutor data that indicates standard practices for treatment of a patient. Generating response data includes generating response data based on the tutor data.

In some of these embodiments, the tutor data includes a tutor cognitive component that describes a tutor's awareness of prior responses and ability to convey information in response to queries.

In other sets of embodiments a computer readable medium and an apparatus improve care delivery using one or more of the above methods.

BRIEF DESCRIPTION OF THE DRAWINGS

The present invention is illustrated by way of example, and not by way of limitation, in the figures of the accompanying drawings, in which like reference numerals refer to similar elements and in which:

FIG. 2 is a flow diagram that illustrates at a high level a method for training medical personnel according to an embodiment;

FIG. 9 is a flow diagram that illustrates at a high level a method for a virtual patient cognitive agent, according to an embodiment; and FIG. 10 is a flow diagram that illustrates at a high level a method for a virtual tutor cognitive agent, according to an embodiment.

DETAILED DESCRIPTION

Figure 1:
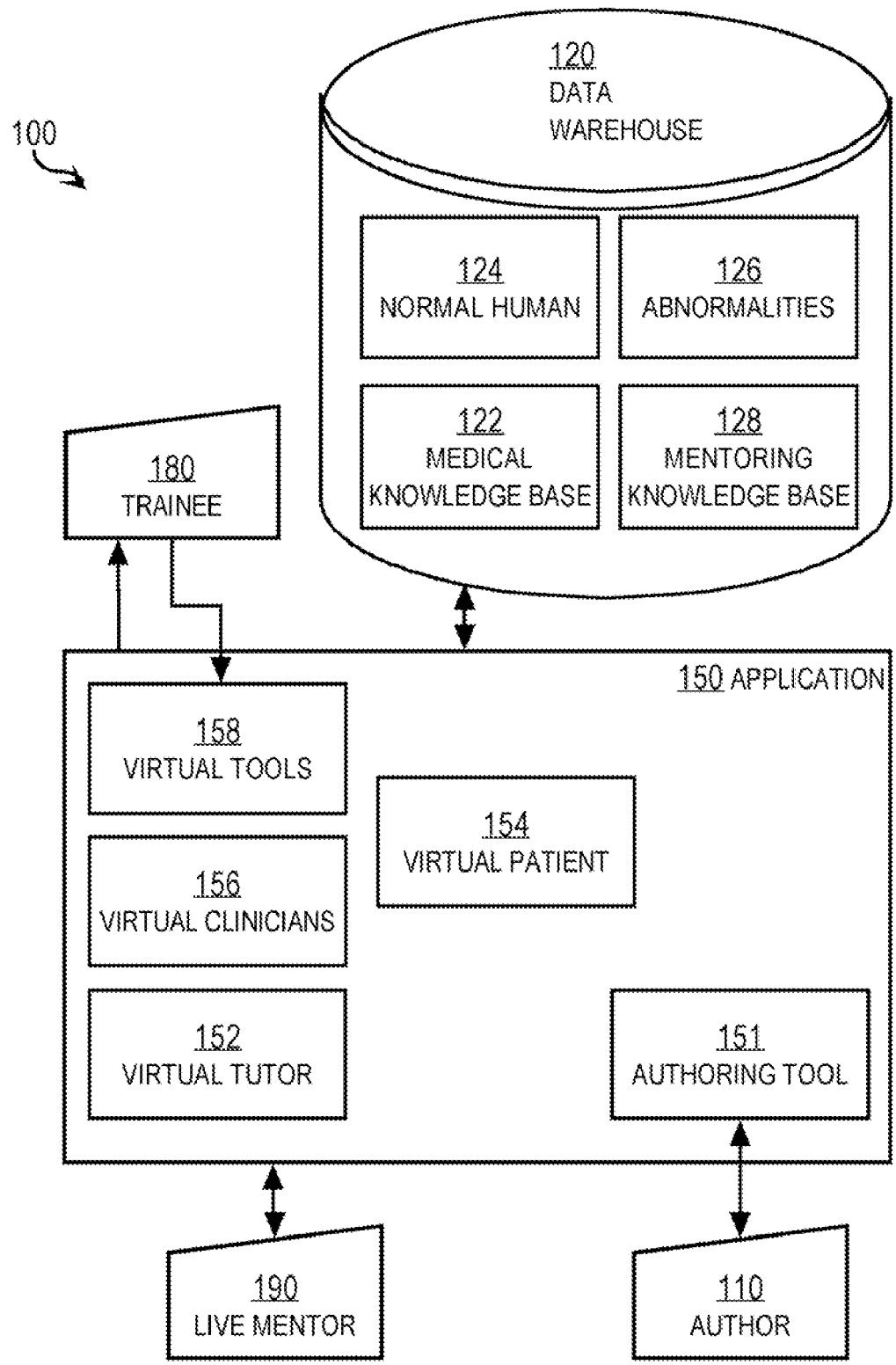
FIG. 1 is a block diagram that illustrates a virtual tutoring system at a high level, according to an embodiment.

A method and apparatus are described for delivering medical care by improving decision-making skills of medical personnel. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Embodiments of the invention are described in the context of teaching medical residents to use cognitive skills in treating human patients, but the invention is not limited to this context. In other embodiments, other medical personnel such as nurses, veterinarians and technicians are taught to deal with patients, either human or other animal. In some embodiments, a system is used by any medical trainee, including a medical professional who has been previously trained. In some embodiments, a system is used for teaching, for assessing either by a third party or self both for credentialing and not. In some embodiments, a virtual patient or virtual tutor is authored based on an actual patient and used by one or more physicians to accumulate data about the actual patient, exchange data about the actual patient, develop a complex diagnosis protocol for the actual patient or similar patients, and experiment with a treatment procedure for the actual patient or similar patients, or to perform some combination of activities to support the delivery of medical care to the actual patient or similar patients.

In the illustrated embodiments a virtual patient is used. The use of a virtual patient provides a great advantage, because no predefined protocols are needed for a trainee to interact with the virtual patient. The virtual patient represents physical conditions of a patient that can be discovered by a trainee no matter what sequence of tests or procedures the trainee orders. If the trainee causes a change in the physical condition of the virtual patient, that change is recorded and later tests show the effects of the change wrought by the trainee.

Another advantage of the virtual patient that describes measurable attributes is that it does not require and is not limited by a label or human conceptual model superimposed on its existence. An abnormal mass has size, position, density, temperature, and differing opacity at different wavelengths of electromagnetic or acoustic waves or other imaging phenomena. It is not a priori a cancer or a sprain. Combinations of diseases can be simulated and new diseases can be simulated as readily as established diseases.

Working in concert with the virtual patient in the illustrated embodiment, is a virtual tutor that may employ any of several pedagogical approaches to teaching the trainee the medical knowledge represented by that mentor. The approach chosen depends on the state of the trainee and experience of live mentors as acquired using knowledge based engineering principles. This provides a great advantage over other training systems that take a single approach, such as preventing the trainee from deviating from a set of one or a few predefined protocols. In the illustrated embodiment, at least three pedagogical approaches or "rules," are allowed, alone or in combination: 1] a null response: 2] a guided response; and 3] an intervention. In a null response rule, no tutor or mentor response, or a limited response, is given to a trainee, whereby the trainee learns through self-discovery. In a guided response rule, the trainee is directed to consider a deficiency in a requested action, an alternative action, or a topic in a knowledge base, or search elements to use in a search engine, or some combination, based on knowledge in a medical knowledge base. Some aspects of learning, through searching topics in a search engine, are included in the concept of self-discovery. In an intervention rule, an action requested by the trainee is modified or prevented by the mentor or virtual tutor based on knowledge in the medical knowledge base. In other embodiments, more or fewer pedagogical rules are allowed. In some embodiments, the virtual tutor is used to evaluate and tailor mentoring rules and curriculum to one or more user needs.

1. Structural Overview

FIG. 1 is a block diagram that illustrates a virtual tutoring system 100 for improving the delivery of medical care at a high level, according to an embodiment. More details are provided in a later section. System 100 includes a data warehouse 120 which provides data storage and management for information used by the system 100 and includes an application 150 that utilizes the data in data warehouse 120 and input from an author and trainee to teach cognitive skills to the trainee. In the illustrated embodiment, input from a live mentor is also included. While the author, trainee and live mentor, per se, are not elements of the system 100, one or more input/output (I/O) devices 110, 180, 190 to prompt and receive input from them are part of the illustrated system 100.

Data warehouse 120 is any non-volatile storage device or system known in the art, including a single node or multi-node network storage system and one or more databases with database servers. In the illustrated embodiment, data warehouse 120 includes a medical knowledge base 122, data describing a normal human 124, data describing abnormalities 126, and a medical mentoring knowledge base 128, also called a pedagogical knowledge base. Medical knowledge base 122 is any medical knowledge base known in the art, and may include facts, decision trees, inference rules, and any other form of medical knowledge known in the art for training or other purposes, for example, as described in more detail in a later section. A database of medical knowledge is called "ontological" data and an object oriented medical knowledge database comprising multiple "ontological classes" is described in more detail in a later section. In some embodiments, the ontological data is stored as concepts and event scripts connected to a natural language processing system. As is well known in the field of artificial intelligence, an event script is a collection of events connected through causal or temporal links, which progress through a series of steps carried out by a set of agents or engines.

The data describing a normal human 124 may be any data, including diagrams, photographs, vital statistics, and imagery data. In some embodiments, data 124 for normal human includes visible human data as described in more detail in later sections. In an illustrated embodiment, normal human data 124 includes medical cross-sectional images from a visible human, regions of cross-sectional images that are associated with anatomical features, and volumes within a human defined by a mesh of three dimensional coordinates called a polymesh associated with anatomical units. As described in more detail in a later section, normal human data also includes mappings that relate a polymesh and an image region with an anatomical class defined by physical properties and processes of anatomical units as stored in the medical knowledge database 122. In an illustrated embodiment, the physical properties and processes in an anatomical class may include any or all, but are not limited to, the following: size, location, anatomical relationships (e.g., anterior to), electromagnetic imaging characteristics, metabolic function, response to perturbations, and evolution with time.

The data describing abnormalities 124 may be any data describing diseased or damaged anatomical units, including cross-sectional images of tumors, abscesses, foreign objects, and data describing toxins or other byproducts of abnormal processes, including their progression with time. In some embodiments, some progressive abnormalities are described by event scripts also used by a natural language processing system.

According to illustrated embodiments of the invention, disease processes are best viewed as abnormalities with anatomic, physical, pathological and physiological attributes. An abnormality eventually becomes described, and thus diagnosed, by a trainee as it is investigated by modalities that reveal these attributes. The attributes are discoverable by the trainee by virtue of their local, regional and systemic characteristics and the investigative capabilities of diagnostic questions, examinations, devices and procedures available to the trainee. For example, an abnormality in the lumen of the colon, such as a colon cancer, has physical "visibility" attributes relating to the human eye aided by an endoscope, X-ray and magnetic imaging, as well as a pathological "vascularity" attribute that is indirectly related to X-ray visibility if intravenous (IV) contrast is administered. A device employed to visualize the abnormality must have characteristics that correspond to a patient abnormality attribute for a result to be generated for the trainee.

The mentoring knowledge base 128 is any data that describes pedagogical approaches to teaching medical cognitive skills. In an illustrated embodiment, mentoring knowledge base 128 includes a set of pedagogical rules such as the null response rule, the guided response rule set, and the intervention rule set, and means for determining which to use, as described in more detail in a later section.

Application 150 is a process, such as a process based on computer instructions executed by a one or mores processors on one or more general purpose computers, as described in more detail in a later section. Data used for process 150 comes from data warehouse 120 and input/output (I.O) devices 110, 180, 190 for an author, trainee and live mentor, respectively. Although drawn as three separate I/O devices, in other embodiments, more or fewer I/O devices may be used. Application 150 performs steps in a method for improving cognitive skills of medical personnel, as described in more detail below with reference to FIG. 2.

In an illustrated embodiment, application 150 includes other sub-processes that divide the work of application 150. The other sub-processes, sometimes called "agents," or "engines," may execute in parallel or sequentially or in any combination. The sub-processes include an authoring tool 151, one or more virtual tutor agents 152, a virtual patient 154, one or more virtual clinician agents 156 and one or more virtual tools 158, all of which are described in more detail in a later section.

The authoring tool 151 performs steps that allow an author to develop an instance of a virtual patient based on the normal human data 124 and zero or more items from abnormalities data 126, as described in more detail in a later section. In some embodiments, the authoring tool generates an instance of a virtual patient automatically based on one or more configured parameters. In some embodiments, authoring tool 151 performs steps to generate the normal human data 124 and abnormalities 126 and agents, such as the virtual tutor 152, the virtual clinicians 156, and the virtual tools 158. In some embodiments, authoring tool 151 performs steps to generate portions of the medical knowledge base 122 and the mentoring knowledge base 128.

The virtual tutor agent 152 provides responses from a virtual tutor to a trainee based on a pedagogical model (a set of pedagogical rules as described above, also called a mentor model) and a pedagogical logic processor and one or more tutor personalities, representing different medical specialties or differing opinions within the same specialty, as described in more detail below. In some embodiments, described in a later section, the virtual tutor includes a cognitive component to simulate the mental and verbal processes that affect what is revealed by the virtual tutor in response to prodding by the trainee. In some embodiments, the pedagogical knowledge base 128 is also updated in response to input from the live mentor, if present, through I/O device 190. In such embodiments, input from the live mentor is captured in a pedagogical knowledge acquisition process, reviewed by knowledge engineers and validated or evaluated in a pedagogical knowledge validation process in consideration for updating the mentoring knowledge base 128 or medical knowledge base 122, or both, as described in more detail in a later section. A mentor or virtual tutor only intervenes if it is enabled to do so. In some embodiments, one or both are disabled.

The virtual patient object 154 stores data for the instance of the virtual patient and includes functions that retrieve that data or change the state of the instance of the virtual patient in response to actions on the virtual patient by one or more virtual clinician agents and to modify the properties of the instance of the virtual patient based on the passage of time. In some embodiments, described in a later section, the virtual patient includes a cognitive component to simulate the mental and verbal processes that affect what is revealed by the virtual patient in response to prodding by the trainee.

The virtual clinician agents 156 act on the current instance of the virtual patient based on actions requested by the trainee. For example, if a trainee asks for vital signs, a nurse practitioner virtual clinician interacts with the current instance of the virtual patient to obtain the vital signs data. If a trainee directs that an arm be amputated, and a mentor and the virtual tutor allow it, or are disabled, a surgeon virtual clinician interacts with the current instance of the virtual patient to remove the designated arm.

Virtual tools 158 are the means by which the trainee indicates the actions that are to be performed. In illustrated embodiments, the virtual tools are presented to a trainee through a user interface, using such interactive elements as icons and data forms. Virtual tools represent vital signs measurements, surgical procedures, diagnostic tests, equipment and other tools to be used in actions to be performed. In an illustrated embodiment, the trainee is presented with icons representing tools for asking a question of the instance of the virtual patient; requesting file data about the instance of the virtual patient; requesting a diagnostic test be performed on the instance of the virtual patient; requesting an imaging procedure be performed on the instance of the virtual patient; requesting a surgical procedure be performed on the instance of the virtual patient; and prescribing a treatment for the instance of the virtual patient, including drug and physical therapy. In some embodiments, the user interface includes a natural language processor; and the trainee may indicate the actions and obtain some responses using natural language, either typed or spoken or both, depending on the implementation. The selected actions are then performed by the appropriate virtual clinician 156.

In some embodiments, application 150 includes a session manager that controls interaction with one user (such as a trainee, author, or live mentor) at an I/O device and a session synchronization server that coordinates interactions with other users (e.g., other trainees and live mentors) as shown in more detail in a later section, with reference to FIG. 3B. In some embodiments, application 150 includes a domain model and domain logic processor that runs scripts for the various agents and database servers, as shown in more detail in a later section. In an illustrated embodiment, the application 150 also tracks trainee knowledge with a trainee model. The trainee model keeps track of user preferences, trainee history and profiles, logs user actions, or evaluates user performance using objective measures, or performs some combination of these or other actions.

2. Functional Overview

FIG. 2 is a flow diagram that illustrates at a high level a method 200 for improving cognitive skills of medical personnel according to an embodiment. Although steps are shown in FIG. 2, and subsequent flow diagrams, in a particular order for purposes of illustration, in other embodiments, the steps may be performed in a different order, or overlapping in time, in series or in parallel, or one or more steps may be omitted. More detailed steps corresponding to an embodiment of method 200 are described in a later section.

In step 210 normal patient data is received, for example, from visible human data stored in normal human data 124 in data warehouse 120. In some embodiments, receiving normal data includes selecting normal data based on gender, age, race, or environment or some combination. In some embodiments, receiving normal patient data includes receiving data from an expert human author through an I/O device.

In step 220, abnormality data is received. In some embodiments the abnormality data is received from an author, for example, some of abnormalities data 128 is retrieved through I/O device 110 and selected or modified by an author at I/O device 110. For example, in some embodiments, abnormality data is generated by specifying deviations from normal values of one or more properties associated with an anatomical class. In some embodiments, data stored in data warehouse 120 is retrieved as the abnormality data during step 220.

In some embodiments, the abnormality is a side-effect of something else. For example, if a normal human is given a Heller myotomy during an intervention (his lower esophageal sphincter is surgically cut), he'll end up with GERD.

In some embodiments, a patient has only hypochondria and no physical abnormality. This might be an interesting training case because a trainee might start intervening thinking that the trainee is expected to do something.

In some embodiments, the abnormality is generated automatically. The system knows the parameter ranges for patients and with some constraints mix and match features to create a large population of VPs automatically.

In step 230 an instance of a virtual patient is generated as described in more detail in a later section. In some embodiments, steps 210, 220, 230 are performed using authoring tools 151.

In step 240, action data is received from a trainee, for example by selecting virtual tools 158. In some embodiments, step 240 includes typing or speaking the actions in natural language; and a natural language processor interprets the input for use by the application 150.

In step 250 a response is generated. In an illustrated embodiment, step 250 includes steps 252, 254, 256, 258. In step 252 the application 150 interacts with a virtual tutor 152. For example, for a minimal guided response mode, during step 252 the virtual tutor 152 validates the action to determine whether the trainee provided valid information to perform the action and sends feedback to the trainee. For example, if the action indicates an arm be amputated, the validation step ensures that either the right arm or the left arm is specified. As a further example, the virtual tutor rates the action as good, bad or neutral and sends that rating back to the trainee as feedback. The virtual tutor in this example allows the action to proceed as intended by the trainee. Validation actions made by virtual tutors are based upon inferences which themselves are based upon the history of states of the virtual patient and medical knowledge 122 accessible to a virtual tutor 152.

As the trainee takes actions within the simulation, compartmentalized agents observe the actions and determine if data discovered by the trainee caused one or more of their rule-sets to become satisfied. Some rule-sets produce visible data seen by the trainee as described below.

Some rule-sets propose, prove or disprove an inference, thus placing an inference and its attributes into working memory. These working memory inferences are not visible to the trainee, but are visible to system agents, such as virtual tutors for use in comparative purposes, and to agents of a virtual patient. An inference may represent an abstract concept (higher in the hierarchy of knowledge) or concrete concept (the terminal child in the hierarchy), and may indicate either a diagnosis, such as chronic gastrointestinal blood loss (abstract) or cecal adenocarcinoma (concrete), or an action including a diagnostic test or intervention, such as removal of a portion of intestinal tract (abstract) or appendectomy (concrete). A virtual tutor gathers the knowledge in stored memory about best practices. The virtual tutor observes the trainee actions and makes inferences and then determines if future trainee actions are also consonant with those inferences. Thus any subsequent trainee action is either discordant or concordant with the list of working memory inferences substantiated from previous trainee actions. If concordant actions are taken by the trainee, then the action is evaluated as appropriate. Conversely, discordant actions taken by the trainee are interpreted as actions that had no proposed or proven inferential support and thus are evaluated as inappropriate. Depending upon the pedagogical design of the simulation (implemented, for example, in a cognitive agent for the virtual tutor), these assessments are used for solicited or unsolicited mentor feedback, such as for mentor intervention to intercept a trainee action in order to prevent it from occurring (preemptive error correction), for strategies to allow the trainee to self-discover an answer to a mentoring request at any point in the simulation, or for mentor assessment of trainee performance. It is noted that experienced mentors' responses vary from pure content to open-ended questions that allow the trainee to determine the correct next action using the trainee's own knowledge and actions to obtain additional knowledge.

In step 254, the application 150 interacts with a live mentor through I/O device 190 to receive additional feedback. In some embodiments of step 250, step 254 is omitted. In some embodiments, feedback received from a live mentor is used to update the mentoring knowledge base 128.

In step 256, the application 150 interacts with a virtual clinician 156 to execute the action requested by the trainee and allowed by the virtual tutor and live mentor, if present and enabled. In an embodiment depicted below, the application 150 creates an instance of a virtual tool (e.g., a CT scan device) and creates an instance of a virtual clinician (e.g., a radiologist) to wield it. The virtual clinician processes the action by operating on the virtual patient with the virtual tool to retrieve the data provided by that tool. For example, the virtual clinician retrieves from the virtual patient a CT scan of a certain portion of the virtual patient. If the portion scanned transects only polymeshes associated with normal properties, a normal image is provided. If the portion scanned transects a polymesh associated with abnormal properties, an image with an abnormality imposed is provided.

It has been found that compartmentalizing the specialty decision-making into specialized agents (e.g., general surgeon or internist virtual clinicians) allows an author to think within specialty, expediting authoring. In addition, this design improves manageability of content and logic and minimizes logic conflict. In various embodiments, the specialized agents interact to minimize conflicts, or emphasize them, or manage the differences where they are important, or some combination.

In step 258, the virtual patient is updated. For example, if no affecting action is taken, such as during the CT scan, the patient's abnormality advances by the amount of time associated with the action. If an affecting action is taken, such as an amputation, the data in the virtual patient is updated to reflect the action, such as by removing the tissue in the amputated arm from the virtual patient.

As a result of step 250, a response is generated, such as the CT scan retrieved by the clinician from the patient and the update to the patient. In an example depicted in more detail below, the response is sent to the virtual tutor 152 to add any comments based on the CT scan. A response from the virtual tutor 152 is added to the response data. In some embodiments, the comments are produced by a natural language generator. In some embodiments, a response based on the result from the virtual patient is received from a live mentor. In some of these embodiments, feedback received from a live mentor is used to update the mentoring knowledge base 128.

In step 280 display data is derived from the response data and presented to the trainee. For example the CT scan is presented to the trainee, with any comments from the virtual or live mentor in some embodiments, and without some or all of those comments in other embodiments. In some embodiments, the comments produced by a natural language generator are displayed as text or are spoken, depending on the implementation. Control then passes back to step 240 to allow the trainee to input a subsequent action.

In step 290, data based on the response is presented to a live mentor. For example, the CT scan and comments from the virtual tutor are displayed for the live mentor. In some embodiments, the response includes assessment of the trainee's performance. In some embodiments, during step 290, the live mentor modifies the comments of the virtual tutor, including any assessment of the trainee's performance. In these embodiments, the modifications are not only presented to the trainee, but also captured by the pedagogical knowledge acquisition process, reviewed, validated and used to update the pedagogical knowledge base (e.g., mentoring knowledge base 128). Final assessments are recorded in a log in the trainee's profiles.

There are several advantages to this approach. (1) It reflects clinical reality. (2) It allows the author to more easily design devices and investigative modalities in a way such that the device will discover an abnormality independently, thus automatically allowing internally consistent "bookkeeping" and avoiding conflicts in a simulation. (3) It allows the trainee to choose any investigative modality and to have returned a plausible result coherent with other findings, even though the trainee action may not have been anticipated by the author. (4) Lastly, if an abnormality and its attributes are removed by the trainee by some procedure or treatment, a procedure that previously demonstrated the abnormality would subsequently not visualize it. Thus the instance of the patient changes dynamically in response to actions taken by the trainee to alter its state. It is believed that this approach to creating a disease process corroborates accepted wisdom in knowledge based systems that the correct choice of conceptualization for a real world problem can greatly facilitate its computer-based solution

3. Example Embodiments

In the following, the structures of system 100 and steps of method 200 are described in more detail with respect to example embodiments. These example embodiments are object-oriented or event-oriented processes that are implemented in hardware or software. In object-oriented processes, an object class (hereinafter "class") is a set of parameters ("attributes") and functions ("methods") that operate on values for those parameters. The functions are often implemented as software scripts that are compiled and executed as needed. The set of parameters and functions are the characteristics of the class. An object is an instance of the class that includes particular values for one or more of the parameters. In some embodiments, one or more parameters are other object classes with values corresponding to instances of those classes. In some embodiments, one or more parameters are object classes that represent relationships with other classes. Different classes may be hierarchically related, with subclasses inheriting characteristics from more general supraclasses above them in the hierarchy. In event-oriented processes, scripts represent a sequence of events that can be nested to form more complex events from more simple events.

In some embodiments, OntoSem (Ontological Semantics) ontology is employed (see, Nirenburg, Sergei and Victor Raskin. 2004. Ontological Semantics. MIT Press, Cambridge, Mass., the entire contents of which are hereby incorporated by reference, as if fully set forth herein). This ontology was initially developed to support knowledge-based language processing; but the rich inventory of features (properties) it uses, notably, description of complex events as scripts, has facilitated a smooth extension to include broader modeling and simulation applications. Thus in these embodiments, a single ontology underlies both the medical knowledge domain and the language processing reasoning, which allows smooth integration of the reasoning and the communication capabilities.

In the example embodiments, ontological classes are defined to describe anatomically functional units that are clinically useful in simulating the behavior of a patient to diagnosis and treatment. Conceptually, an ontological class is defined for one or more anatomical structures that function with integral characteristics that are clinically relevant. Ontological classes are determined by defining functional units as they come into play in health and disease, tailored especially for simulating patient response and case management. Some functional units describe normal and abnormal biochemical and biomechanistic pathways. For example, abnormal pathways describe disease processes that: a) have detectable starting points, b) develop and change over time, c) can be diagnosed from detectable signs, symptoms and tests, d) respond to intervention, and e) interact with any number of other processes. An ontological class may also represent non-anatomical structures, e.g. the patient's living conditions, familial relationships and medical history, among others. Ontological classes are stored in the medical knowledge base 122.

Ontological classes in a hierarchy represent different levels of granularity for a virtual patient. For example, ontological classes and superclasses are defined to represent a gene, a protein, an organelle, a cell, a group of cells, a tissue, an organ, an organ system, a functional structure, the body as a whole, and a population of multiple bodies. In a more specific example, a group of cells in an area within the liver that function uniformly as hepatocytes define a hepatocyte class. An object of this class defines a group that contains a defined number of cells that function as a hepatocyte unit within a particular liver. A similar region, also within the liver, but having a different function for some clinical purposes define a different class, for example a region that functions as Kupffer cells define an object of a Kupffer class. A liver supra-class provides functions and parameters that are common to hepatocytes and Kupffer cells. A liver object of the liver class includes a hepatocyte object and a Kupffer object and provides values for parameters common to both.

Another clinically useful ontological sub-class for a liver class is a site where a tumor could replace a portion of liver. In a particular instance of this class, i.e., in a liver tumor site object, the portion of the liver is identified and particular characteristics of the tumor are specified. The liver tumor site object is deleted to simulate removal of a tumor by a surgeon; and thus the liver tumor site class is clinically useful for simulations. In some embodiment, ontological classes are written to reflect hierarchies established in the medical profession, such as the National Library of Medicine Subject Headings (NLM MeSH). For any level of granularity, gaps will exist in the knowledge of biological mechanisms. These gaps are bridged by integrating knowledge derived from other knowledge sources, such as from clinical perspectives.

In the example embodiments, a virtual human is a data set including multiple ontological objects that describes functional features of a human. The set of objects represent a sufficient collection of ontological classes to reflect the structure and function of a human as a whole, or in part, as needed to simulate normal or disease processes or both. In some embodiments, the degree of granularity is limited to that needed to support simulation for a particular use. Virtual humans are stored as objects (instances of ontological classes whose functions define the functionality of those classes) and events. For example, the normal human data 124 includes a virtual human expressed as a collection of ontological objects and scripts for evolving and interacting among those objects. Representing virtual humans as a collection of objects and scripts permits extensibility by creating modular components of medical knowledge, which use standard ontological principles and an open-source format. In an example embodiment, anatomical structures to serve as classes are identified by using resources such as the Foundational Model of Anatomy (FMA) (Rosse, C. and J. L. V. and Mejino, "A reference ontology for bioinformatics: The Foundational Model of Anatomy," Journal of Biomedical Informatics, 2004, the entire contents of which are hereby incorporated by reference as if fully set forth herein).

In the example embodiments, ontological classes also represent virtual tools 158 and virtual agents, including virtual clinicians 156 and virtual tutors 152. A trainee within a user environment uses virtual tools to investigate and modify data within a virtual human. Virtual clinicians encapsulate the functionality used to perform an action or set of related actions requested by the trainee, for example, using scripts. Virtual tutors encapsulate the functionality used to guide a trainee in the diagnosis and treatment of a virtual human. These ontological classes are described in more detail below in the context of their functions.

Ontological classes are defined to contain attributes and methods or event scripts or both necessary to completely describe a patient including: the entire medical, family and environmental history of the patient; certain components of physical examination; body fluids composition; visibility of certain components using imaging; how time and interventions might affect these components; and how these additional data might be linked to components in an original data set. Ontological class scripts provide operational rule sets that govern how an instance changes in response to interventions and time.

In the example embodiments, ontological classes, and thus ontological objects, do not contain image data. Thus, a virtual human does not include image data. In these embodiments, ontological classes do not necessarily represent anatomical structures visible in a particular image, for a variety of reasons. For example, the image may be produced by a measurement system that does not detect objects in the class or the image may be obtained at a given level of granularity that does not show objects in the class, or there may be no image available. The anatomical units in some classes might in reality intersect with other anatomical structures, contain other structures, and be composed of non-contiguous structures. Instead, appropriate mapping associates stored image data with one or more ontological objects.

In the example embodiments, image data constitutes visible human data. Visible human data is a finite collection of uniformly sized units of data, e.g., picture elements (pixels) and volume elements (voxels) representing different spatial positions such as along a cross-section or within a volume. Each unit has one or more values (e.g., a single grayscale value, or a triplet of red-green-blue values called RGB values), which, when displayed, convey information demonstrating the anatomy of a normal human at the spatial position represented. The visible human data is primarily image data obtained from measurement systems, including integrating images such as obtained from optical and X-ray exposures, and cross-sectional images such as obtained from computer aided tomography (CAT) scans, also called CT scans, and nuclear magnetic resonance (NMR) scans, also called magnetic resonance imagery (MRI). In some embodiments, visible human data includes but is not limited to data from one or more funded projects with such names as "Visible Human" and "Virtual Human." In some embodiments, visible human data excludes data from these funded projects.

In some example embodiments, one or more images in the visible human data are segmented into regions that have anatomical meaning. For example, segments of an image that represent the liver are distinguished from segments that represent other tissue, such as bone, muscle, heart, and lungs. In various embodiments, an author segments visible human data through manual segmentation or computer assisted segmentation, or both. It is anticipated that, as technology improves, segmentation will become a more automated computational process. In some embodiments, segmentation is completely automatic. In some example embodiments, the segment boundaries are combined across one or more images to form polymesh data. The polymesh data describes a three dimensional surface of a volume in a virtual human that operates as a boundary of an anatomical unit.

Figure 3A:
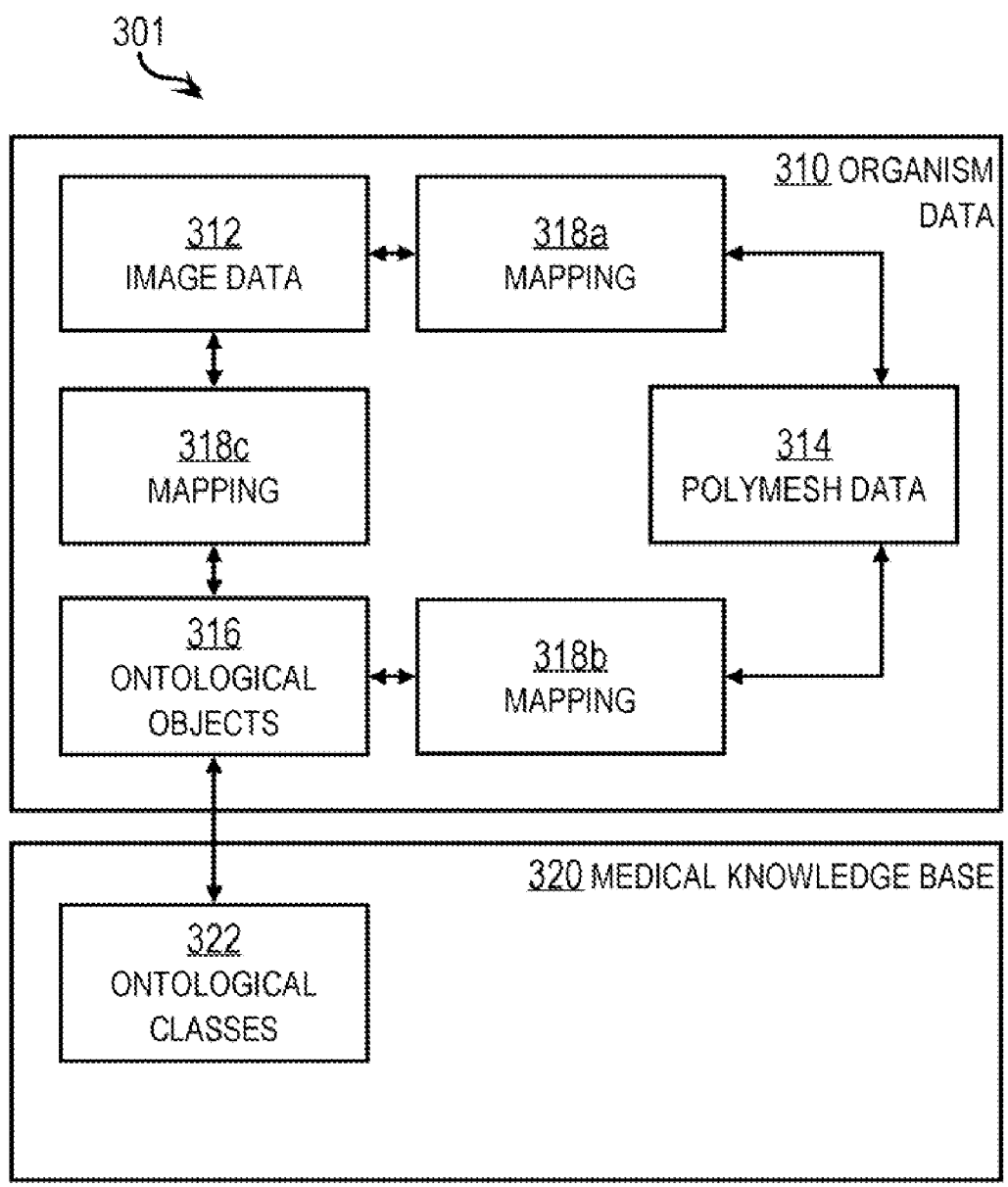
FIG. 3A is a block diagram that illustrates organism data that is used for representing an organism in the system, according to an embodiment

In some example embodiments, the normal human data 124 includes the virtual human, the visible human, the polymesh data, and mapping data that relates these data to each other. FIG. 3A is a block diagram that illustrates organism data 310 that is used for representing an organism in the system, according to an embodiment. The normal human data 124 and the abnormalities data 126 stored in data warehouse 120, and the virtual patient data 154 formed by the application 150 include examples of organism data 310. In some embodiments, one or more instances of the virtual patient data 154 are also stored in the data warehouse 120. In some embodiments, described in more detail below, the virtual patient also includes cognitive components that describe a patient's awareness of symptoms, history of behavior and ability to convey information in response to queries.

The ontological classes 322 for the organism are stored in the medical knowledge base 320, such as the medical knowledge base 122 in data warehouse 120. The organism data 310 includes ontological objects 316, which are instances of the ontological classes with specific values for the parameters of the class. The organism data 310 includes image data 312, which represent the various integrated and cross-sectional views of the organism collected by various measuring systems. The organism data 310 also includes polymesh data 314 that describes the surfaces of volumes that are treated as a boundary of an anatomical unit at some level of abstraction. Subsets of data can be designed and extracted for the accomplishment of specific tasks.

The organism data 310 also includes mapping data 318a, 318b, 318c (collectively referenced hereinafter as mapping data 318). The mapping data 318 includes data that relates entries in the other data to each other.

For example, mapping data 318a relates entries in the image data 312 to entries in the polymesh data 314, which is easily formed as the polymesh data 314 is generated from the image data 312. In some embodiments, the polymesh data 314 is stored with the image data 312. In these embodiments, the mapping 318a is trivial and accomplished by any of several methods, including juxtaposition of each element (e.g., voxel) of the polymesh data 314 to the associated elements (e.g., pixels) in the image data 312, and pointers between the voxels and a set of pixels, among others.

Mapping data 318b relates entries in the polymesh data 314 to objects in the ontological objects data 316, which are readily determined because the polymesh data often represents anatomical features that are also ontological classes at some level in the hierarchy of ontological classes. In some embodiments, the mapping 318b relates polymesh data to ontological classes 322 and those mappings are inherited by the ontological objects 316. In the illustrated embodiment, the mapping data includes mapping data 318c, which relates objects in the ontological objects data 316 to entries in the image data 312. In some embodiments, the mapping 318c relates ontological classes 322 to the image data 312 and those mappings are inherited by the ontological objects 316. The mapping 318c is readily formed based on the mapping 318b between the ontological objects and the polymesh data, and the mapping 318a between the polymesh data and the image data. In some embodiments in which the polymesh data 314 is stored with the image data 312, mapping 318b is omitted.

In the example embodiments, the image data 312 includes the visible human. The visible human is a National Institutes of Health (NIH) sponsored project in which several complete humans were completely CT and MRI scanned and then serially sliced into a set of corresponding detailed anatomic images.

In an illustrated embodiment, an OntoSem ontology is defined. The OntoSem ontology includes classes of objects (e.g., drug, cell) and events (e.g., colon-cancer, perform-surgery) in the world. Example relations include agents, e.g., the agent of a "perform-surgery" event class is a "surgeon" class). A class for the event "colon-cancer" reflects a general-domain granularity of knowledge acquisition, prior to medical specialization. In some embodiments, all classes are in a single medical domain ontology without a medical specialization subclass. A class shows inherited properties. For illustration, one of two lines of inheritance for "colon-cancer" in an embodiment is described. The "colon-cancer" class inherits from a "cancer" class which inherits from a "non-communicable-disease" class which inherits from an "animal-disease" class which inherits from a "pathologic-function" class which inherits from a "biologic-function" class which inherits from an "animal-living-event" class which inherits from a "living-event" class which inherits from a "physical-event" class which inherits from an "event" class which inherits from an "all" class at the root of the OntoSem ontology.

The OntoSem ontology is fundamentally different from most other "ontologies" in its emphasis on rich property-based descriptions that are not present in the many hierarchical trees of words or concepts available both within the medical domain (e.g., Unified Medical Language System [UMLS]) and outside of it (e.g., WordNet). Some such ontologies include properties, but their inventory and application is more limited. Concepts in OntoSem are connected hierarchically through subsumption relations, so that properties defined in ancestor concepts (metaclasses) are valid in the descendant concepts, unless overtly overridden. OntoSem permits multiple inheritance: for example, animal-disease class inherits both from medical-event class and from pathologic-function class. At the time of this writing, the OntoSem ontology contains about 8,200 concepts (events, objects and properties), with, on average, 16 properties each. The ontology includes both general purpose and biomedicine concepts.

OntoSem supports the encoding of complex events as scripts, which represent typical sequences of events and their causal and other relationships. Scripts provide information that is very useful in general reasoning, natural language processing and medicine, including molecular biology. Scripts represent how individual events may hold well-defined places in routine, typical sequences of events that happen in the world, with a well-specified set of objects that fill the different roles throughout that sequence. For example, if the sequence of events describes a colonoscopy, the participants will include the physician carrying out the procedure, the patient, and any number of other medical personnel; the tools will include the colonosope, various monitors and anesthesia; other props will include the operating table and medical gloves and gowns; events will include anesthetizing the patient, carrying out various procedures with the colonoscope; and so forth. Event scripts can contain subscripts (e.g., the scripts of prepping and anesthetizing a patient), and they can be more or less fine-grained, depending on the reasoning required by a given application. The component events are often optional; they may stand in a disjunctive relation with some others (that is, of several components only one may actually be realized in a particular instantiation of the script); and their relative temporal ordering may be partial.

Component events in a script have a special status. They are not regular instances of classes to which they are related by name. Their semantics are different from those of the general classes to which they are related by name. Thus, the event of anesthetizing a patient as part of a colonoscopy script involves constraints different from those in an anesthetize class.

The contents of scripts included in classes are driven by the needs of simulation, meaning that they typically do not represent all known molecular mechanisms and that they may be abridged for simplicity in embodiments where detail is not needed. For example, the precise path of the tyrosine kinase biochemistry may or may not be necessary even though it is known that there is an array of biochemical pathways. However, many embodiments that use bridged versions also use the accurate beginning and ending biochemical structure nomenclature so that if a finer granularity script is later required for new simulations, or new relevant knowledge is discovered, the finer granularity script can be incorporated accurately and easily in other embodiments. Example uses of event scripts are described in a later section.

In an illustrated embodiment, subject matter experts (a biochemist in molecular genetics, a physiologist with molecular expertise, a diagnostic and therapeutic clinician, and a radiologist) follow two complementary cross-level perspectives to generate multiple hierarchies of objects and events. The first perspective is from the gene up into the organism ("gene-up"); and the second perspective is from population medicine down into the organism ("population-down"). The complete spectrum of granularity levels thus produced extends through gene, nucleus, cell, tissue, organ, organ system, body and population. Several databases are used as guides for the structured content of the functional units. For biomechanistic information, medical school curriculum resources and ProteinLounge™, a large dataset of biochemical pathways and associated information organized in a useful format, are used. For population medicine, clinical knowledge, Cochrane Reports and other useful National Library of medicine (NLM) references are used, in some embodiments. For anatomical information, the FMA data set is used.

In step 210, normal patient data is received. As described above, step 210 includes receiving normal human data 124 from data warehouse 120. In the example embodiments, step 210 includes forming the ontological classes 322 and normal human data 124 and storing the normal human data 124 in data warehouse 120. In these embodiments, a medical knowledge author forms and stores the ontological classes 322 based on image data 312 and polymesh data 314. A normal patient author, or an automatic process, uses those classes to form an instance of a virtual normal human as ontological objects 316. The same ontological classes can be used to form other normal humans. The following sequence is used by medical knowledge authors in an example embodiment to create ontological classes representing normal anatomically functional units:

author obtains visible normal human data 312;
author segments visible normal human data into a collection of anatomical regions;
author creates anatomical polymesh data 314 from anatomical region;
author maps anatomical region to anatomical polymesh to form 318a;
author creates empty ontological class within classes 322 from anatomical region;
author maps anatomical region of image data 312 to ontological class as part of 318c inherited by objects 316;

author maps anatomical polymesh to ontological class as part of 318*b* inherited by objects 316;

author inserts ontological class into hierarchy of ontological classes 322;

author relates ontological class to other ontological classes;

author scripts function data into ontological class;

author populates ontological class with static property data; and author repeats process until all anatomical regions are complete and ontological classes 322 are complete.

In the example embodiments, an instance of a virtual human is generated during step 210. The following sequence is used by a normal patient author, or automatic process, to create an instance of a virtual normal human:

author conceptualizes virtual normal human;

author creates instance of virtual human;

author populates virtual human with objects 316 from normal ontological classes 322;

author populates or modifies properties of normal ontological classes with local instance property data in objects 316;

author populates virtual human with global instance property data in objects 316;

author inserts objects 316 and mappings 318 and data 312, 314 as instance of virtual normal human 124 into data warehouse 120.

The virtual normal human is used in the process of creating virtual abnormal human to serve as a virtual patient.

In an illustrated embodiment, specific structures and functions of a single organ, the stomach, is used to define at least part of the virtual normal human. The classes for this embodiment include: Cell of Cajal (an intestinal pacemaker cell); gastric mucosa (parietal and antral); gastric wall components; pain fibers; lymphocytes and polymorphonuclear neutrophiles (PMNs), a receptor blocker and agonist (imatinib and Epidermal Growth Factor [EGF]); a hormone (gastrin); a bacterium (*H. pylori*); and several chemotherapy, anti-bacterial, and anti-inflammatory drugs. The classes include event scripts for a set of encoded pathways at the cellular level, including specific metabolic pathways, drug pathways, cell membrane/extracellular function pathways and growth control pathways.

The biomechanisms of a normal Cell of Cajal are encoded as functional units (e.g., OntSem classes). This cell possesses (1) the kit gene, which codes for (2) the transmembrane kit protein receptor, which is constitutively stimulated by (3) extracellular EGF ligand, and through the kit receptor, affects the (4) tyrosine kinase biochemistry, which affects the (5) cell growth cycle mechanisms. These five mechanisms at a given level of granularity are combined to form a clinically relevant pathway, which is encoded within the Cell-of-Cajal class script. This Cell-of-Cajal class script also includes the following facts. (1) The functions of the transmembrane kit protein receptor are properties derived from the kit gene. (2) Functions of the transmembrane kit protein receptor are: to respond appropriately to extracellular EGF ligand binding, to upregulate the tyrosine kinase pathway, and to respond to receptor blockade by downregulating the pathway. (3) The tyrosine kinase pathway exercises control of the cell growth cycle and can up- and down-regulate cell growth. (4) The range of normal constitutive growth behaviors of the Cell of Cajal is defined using observational studies in the pathological literature.

In step 220, abnormality data is received from an author. As described above, step 220 includes receiving abnormalities data 126 from data warehouse 120. In the example embodiments step 220 includes forming ontological classes 322 for abnormalities and forming abnormalities data 126. The following sequence is used by the medical knowledge authors to create ontological classes representing abnormal anatomically functional units. These abnormal ontological classes inherit from normal ontological classes.

Author conceptualizes abnormal human data;

author obtains visible abnormal human data and stores in image data 312 for abnormal organism (if none available, this step is omitted);

author segments visible abnormal human data into collection of abnormal anatomical regions;

author creates abnormal anatomical polymesh from abnormal anatomical region and includes in polymesh data 314 for instance of abnormal organism;

author maps abnormal anatomical region to abnormal anatomical polymesh and adds to mapping 318*a* for instance of abnormal organism;

author identifies normal ontological class from abnormal anatomical region;

author creates abnormal ontological class and adds to classes 322;

author establishes inheritance of abnormal ontological class from normal ontological class;

author maps abnormal anatomical region to abnormal ontological class and adds to mapping 318*c* for instance of abnormal organism;

author maps abnormal anatomical polymesh to abnormal ontological class and adds to mapping 318*b* for instance of abnormal organism;

author inserts abnormal ontological class into hierarchy of ontological classes 322;

author relates abnormal ontological class to other ontological classes;

author scripts event data into abnormal ontological class;

author populates abnormal ontological class with property data to form abnormal objects 316 for instance of abnormal organism; and author repeats process until all abnormal anatomical regions are complete.

In some embodiments, image data 312 and polymesh data are shared among different instances of organism data 310, e.g., the normal human data 124 and abnormalities data 126. In some embodiments the shared data is stored in a common area of data warehouse 120. In some embodiments, some or all of the shared data is replicated in each instance of organism data, e.g., in the normal human data 124 and abnormalities data 126.

In these example embodiments, the author creates the mappings 318. In these embodiments, the mappings created between the ontological classes 322 and objects 316, anatomical regions of images 312, and anatomical polymeshes 314 reside with the image data 312 associated with the mapping. This creates a stationary foundation of data upon which different sets of image data can be utilized to form different instances of organism data 310. The schema of data sets and mappings is shown in FIG. 3A. This schema allows an author to design a normal or abnormal virtual human, or other organism, without the need to sift through volumes of image data. By virtue of the mapping mechanisms, image data is automatically and appropriately associated with the ontological objects that define the virtual organism 316.

In the illustrated embodiment, mechanisms for the common general pathological processes of neoplasia, inflammation, and infection, their evaluation and management, and their effects on the stomach are simulated by the abnormalities data. As an example of the gene-up perspective, the mechanisms and pathways necessary to generate a Gastrointestinal Stromal Tumor (GIST), a tumor of the Cells of Cajal, are established. The effects of an abnormal Cell of Cajal—as by mutation of a kit gene—is encoded using combined lateral selectional constraints on property values from the normal Cell-of-Cajal script. For example, if a "has-object-as-part" property of the Cell-of-Cajal class includes an object indicating "kit gene" with the "status" property holding data that indicates "mutated," then a cascade of events are set off, created from encoded knowledge, that form the following pathway: (1) the mutated kit gene encodes for an abnormal kit protein receptor, which (2) upregulates its response to EGF binding, which (3) upregulates the tyrosine kinase pathway, which (4) upregulates the growth cycle control. The abnormal Cell-of-Cajal class script also includes, as a fact, the range of abnormal growth behaviors of the Cell of Cajal based on observational studies in the pathological literature.

In step 230 an instance of a virtual patient is generated. In example embodiments, a virtual patient includes an instance of a virtual human within a user interface and including zero or more abnormalities.

The following sequence is used by a virtual patient author, or automatic process, to create a virtual abnormal human used in organism data 310 that serves as part of a virtual patient 154. A virtual abnormal human inherits from a virtual normal human. By doing so, many of the tasks necessary to create the virtual human have already been completed. Only those tasks involving the addition of abnormalities and personalized global property data need to be completed.

Author conceptualizes virtual abnormal human;
author creates instance of virtual human as ontological objects 316;
author establishes inheritance for virtual human from virtual normal human;
author populates or modifies properties of normal ontological classes with local property data;
author populates virtual human with objects from one or more abnormal ontological classes;
author populates or modifies objects of abnormal ontological classes with local property data;
author removes appropriate objects of normal ontological classes from virtual human;
author populates objects 316 of virtual human with global property data; and
author inserts virtual human 316, with mappings 218, and data 312, 314 into data warehouse 120 as organism data 310 that serve as virtual patient 154.

In various embodiments, one or more abnormalities within a virtual human are created by: (1) the addition of an abnormal ontological class (e.g., virtual patient has a parasite), (2) the removal of a normal ontological class to represent an abnormality by virtue of the missing normal ontological class (e.g., virtual patient has no leukocytes), (3) the replacement of a normal ontological class with an abnormal ontological class (e.g., virtual patient has a tumor in the liver), or some combination.

The knowledge necessary for the creation of virtual patients is modeled ontologically (e.g., with OntoSem classes). Specific virtual patients and events associated with them (e.g., medical conditions or diagnostic procedures) are represented as time-sensitive instances of ontological concepts in a fact repository, often in the data warehouse 120. The fact repository also provides the basis for comparison of student performance over time and for performance evaluation of both the student and the system itself.

For example, the virtual patient author selects a patient template and supplies an initial state—which includes selecting an abnormality and providing initial biophysical property values. In some embodiments, the author selects specific paths that the patient takes at branch points in the event script: e.g., a biomechanistic disease process is selected to either respond or not respond to stimuli during simulation. For any choices the author leaves unspecified, the system uses a default, random or statistically grounded selection strategy, or some combination. This authoring process sets up the entire data set to fully represent the virtual patient at run-time for an intended purpose. For example, a stomach abnormality that is a tumor-producing gene defect is provided with a starting point, as well as an actual starting size and growth rate selected from a population-derived range of rates. At the outset, this abnormality might not be clinically detectable by the user within the simulation, but the growth rate over time will make the tumor detectable using the diagnostic tools available to the user.

In an illustrated embodiment, an arbitrary segment of the gastric wall of an instantiated virtual patient is populated with an abnormal Cell of Cajal tissue object. The altered pathway is instantiated in this object at initialization to simulate a tumor. The following facts and behaviors occur. The kit protein receptor is clinically discoverable through selective staining techniques on pathological specimens obtained by biopsy of the tumor. Administering a clinically useful drug such as imatinib (a kit receptor blocker), will block the kit protein receptor and result in automatic downregulation of the growth cycle and diminution of growth in the actively proliferating cells. Administering a specific anticancer drug that suspends the growth cycle will result in cessation of proliferation in the actively proliferating cells. Performing hypothetical gene therapy to replace or override a mutated kit gene to create normal function will have a negative effect on proliferation over time. These behaviors are only revealed when a user employs appropriate virtual tools to evaluate or treat the virtual patient, as described in the next step.

In another illustrated embodiment, an abnormality that an author inserts in the stomach of a virtual patient includes a gastric ulcer associated with *H. pylori*. The ulcer, modeled as a segment of abnormal tissue, is simulated by creating a functional unit that contains the entire pathological repertoire of processes in an ulcer, with its own unique, abnormal structure, growth and disrupted function due to *H. pylori*. The ulcer continues to change qualitatively and/or quantitatively in either direction (e.g., it can grow or it can heal) and is detectable through diagnostic procedures and treatable through therapeutic procedures. Modeling this complex process is straightforward because the biomechanisms are well-described, the ulcer involves largely local processes, and the clinical management is well-defined.

In some embodiments, population-based empirical clinical knowledge is used where mechanisms are not so thoroughly understood. Computationally, both explained and empirically observed processes in the same knowledge representation schema are represented by adding non-mechanistic bridging to causal chains in event scripts. These bridges are modeled using population studies and contain stochastic information. In the GIST tumor, the genetic mechanisms that control phenotypic expression are not known, requiring population-based information for complete description. For example, a biomechanism is not known explaining why the tumor has a specific doubling time, so this property is derived from clinical studies. A similar, large arena of unknown biomechanisms relates to systemic symptoms. For example, it is not known when a process causes the symptom nausea. To bridge this gap and automatically produce the symptom, a link between a gastro intestinal structural process and the symptom nausea is established on the basis of empirical clinical knowledge. The bridge is triggered by biological data (e.g., 10 cm diameter tissue in the lumen of a hollow GI organ) and outputs biological data (e.g., stimulate local gastric neurons connected to the nausea center in the brain). This then facilitates autonomous simulation of the symptom nausea when a GIST in the stomach (or more abstractly, when any mass in any hollow GI organ) reaches a requisite size.

At the beginning of a simulation session, the system presents the trainee with a virtual patient about whose diagnosis the trainee initially has no knowledge.

In step 240, action data is received from a trainee. In an illustrated embodiment, the trainee selects diagnostic and treatment options using a menu-based (essentially, multiple-choice) interaction system. In later illustrated embodiments, a natural language-based interaction is used. In the current illustrated embodiment, the trainee selects among virtual tools 158, which are objects to interact with a virtual patient. These interactions may be investigative or interventional. When an investigative virtual tool is employed by the trainee, data is obtained from the virtual patient. When an interventional virtual tool is employed by the trainee, data within the virtual patient is changed. For example, a virtual tool that represents a lab test or a history question reveals data from the appropriate virtual patient data to the trainee (subject to the cognitive functions of the virtual patient, in some embodiments, as described below). A virtual tool that represents a surgical procedure or a medication will change virtual patient data. In the example embodiments, virtual tools are stored as ontological classes, and instantiated as objects when employed by a trainee. Examples of virtual tools include, among others, a medical device such as a colonoscope, a medical procedure such as an exploratory laparotomy, a medical imaging procedure such as a CT scan, a medical lab test such as a complete blood count (CBC) or blood culture, and a medical drug such as penicillin.

The following sequence is used when an author creates an ontological class representing a virtual tool.
  author conceptualizes tool;
  author creates empty ontological class representing tool;
  author inserts ontological class into hierarchy of ontological classes 322;
  author populates ontological class with property data;
  author relates ontological class to other ontological classes; and
  author scripts event data into ontological class.

In step 250 an appropriate response is generated. For example, if the trainee removes an organ surgically in the simulation, this action removes the organ from the data representing the patient. It the trainee performs an imaging test such as a CT scan, then the system provides an appropriate result congruent with the current state of the patient, e.g., after organ removal based on a prior surgical procedure. If the trainee requests an unexpected test or exam that should be normal in this disease, then the system returns a normal result.

A trainee would observe the patient change with time if it were appropriate for the given disease and a correct intervention (or incorrect intervention).

In the example embodiments, step 250 includes steps to interact with virtual agents. In these embodiments, a virtual agent represents either a virtual clinician or a virtual tutor. Each virtual agent may perform at least one of three roles within the user interface. These roles are: (1) to provide the basic functionality to process the interactions requested by the trainee, (2) to provide the trainee with guidance through the user interaction based upon a proscribed pedagogical design, (3) to provide an assessment of trainee actions.

These virtual agents are invoked when needed. For example, a virtual surgeon only becomes active within the user environment when the trainee selects a surgical procedure. There may be any number of virtual agents active in the user interface at any given time. Throughout the course of its existence, a virtual agent monitors the events within the user interface in order to respond appropriately. By encapsulating monitoring and response functions within an object class, an author can not only design new virtual agents with inherited functionality, thus easing the process of authoring, but virtual agents can also be easily interchanged in order to simulate different environments with different characteristics. In the example embodiments, virtual agents are stored as ontological classes. A virtual clinician is a virtual agent that replicates the functionality of a clinician within the user interface by taking on the first role. A virtual tutor takes on the second role or third role or both.

A virtual clinician takes on the first role, for example, by wielding the virtual tools selected. For example, a virtual endoscopist wields the virtual colonoscope; a virtual surgeon performs the exploratory laparotomy, a virtual radiologists performs the CT scan, one or more virtual pathologists performs the CBC and blood culture, and a virtual nurse administers the penicillin.

The following sequence is used when an author creates an ontological class representing a virtual clinician. These virtual clinicians are employed when a trainee requests an action, whether investigative or interventional. They encapsulate the functionality to carry out the requested action.
  Author conceptualizes clinician;
  author creates empty ontological class representing clinician;
  author inserts ontological class into hierarchy of ontological classes 322;
  author populates ontological class with property data;
  author relates ontological class to other ontological classes; and
  author scripts event data into ontological class.

A virtual tutor is a virtual agent that monitors the events within the user interface and proposes, proves and disproves inferences based upon the data currently available. Through the use of these inferences, judgments can be made at a higher level of computation in order to perform clinical decision-making and trainee assessment. Virtual tutors are designed to execute a pedagogical strategy aimed at meeting the educational needs of the trainee as determined by the author's design and an assessment of the trainee's performance. A virtual tutor, like a live mentor, views data the trainee has uncovered and the trainee log of actions, and applies rule sets to reach inference, prediction and assessment conclusions. A cognitive component of a virtual tutor is described in a later section.

During step 250, the virtual patient, its internal network of ontological classes, and the tools to discover information from those classes interact in a manner similar to our understanding of real life. The structure and function and their related properties are resident in the virtual patient similar to real life. The tools to discover that structure and function are designed to detect similar properties seen in real life. The actions employed by the user to effect change in the virtual patient are performed to change properties similar to that in real life. This design strategy produces a realistic simulation, and is consistent with a defined system of concepts and relationships within an ontology that represents our current understanding of anatomy and physiology in health and disease. In response to trainee queries the system returns information stored in the virtual patient that includes history, examination and laboratory results as well as textual and visual study reports that simulate input from consultants. In an illustrated embodiment, the system's responses to the trainee's queries are stored as data in a trainee copy of the virtual patient. At the beginning of the session, the copy is representative of a virtual human without abnormalities. The diagnosis process by the trainee results in a gradual modification of the trainee's copy of the virtual patient. In the case of successful diagnosis, the trainee's copy closely resembles the system's version of the virtual patient that was originally assigned to the trainee.

In some embodiments, the differences between the trainee copy and the system's version are quantified by a virtual tutor and serve as a score or a basis for a score of the trainee's performance.

At any point during the diagnosis of the virtual patient, the trainee may proceed with treatment. In other words, the system allows the trainee not only to issue queries but also to intervene in the simulation, changing property values of objects within the virtual patient. A manipulation of virtual patient data through trainee intervention produces functional or anatomical modifications to the virtual patient, or both. Functional effects include up-regulating, down-regulating, adding or removing a function, and changing the action of a mechanism or pathway, among others. Anatomical effects include changes in physical characteristics of size, shape, radiological and pathological properties, and presence or absence of a structure among others. These effects are manifest as alterations in image representations in some embodiments.

Changes in the status of the virtual patient are represented ontologically in terms of changes in property values in the given instance of the virtual patient. Any single change can induce other changes by triggering a related domain event script. For example, if a gastric neoplasm grows to a certain size, then the event script for nausea is triggered. The nausea script in this example has a time-sensitive development with side effects (e.g., a decrease of patient food intake and resulting loss of weight). The chaining of medical events and their effects is an advantage of modeling a patient biomechanistically, since a script for an event like nausea is much the same regardless of its triggering biomechanism. An important aspect of the virtual patient is its time-sensitive modeling.

In some embodiments, the trainee controls the time steps of the simulation (i.e., controls the "clock"), permitting virtual follow-up interviews, (re)issuing of lab tests, (re)ordering of a biopsy and the like at any given time. Controlling the clock is an advantage for the trainee because events like growth of a neoplasm and weight loss due to nausea are authored to develop at a certain rate. The simulation remains lifelike in that diagnostic procedures are carried out and results are obtained in a time frame appropriate for the corresponding real world procedures.

In an illustrated embodiment, processing in the simulation environment is carried out within the dynamic dependency-directed planning paradigm. In this paradigm, declarative data (e.g., the ontological knowledge about genes, proteins, cells, tissues, organs, organisms, virtual tools, virtual clinicians, etc.) is augmented with procedural attachments (e.g, event scripts) that support automatic modification of data stored in instances of ontological concepts (e.g., virtual patients). These procedures are controlled by Hunter-Gatherer, a processing architecture integrating constraint satisfaction, branch-and-bound and solution synthesis algorithms. See Beale, Stephen, "Hunter-Gatherer: applying constraint satisfaction, branch-and-bound and solution synthesis to computational semantics," Ph.D. Dissertation, Language and Information Technologies Program, School of Computer Science, Carnegie Mellon University, 1997 (Beale 1997a) and Beale, Stephen. 1997b, "Using branch-and-bound with constraint satisfaction in optimization problems," Proceedings of AAAI-97, Providence, R.I., 1997 (Beale 1997b), the entire contents of both of which are hereby incorporated by reference as if fully set forth herein. Hunter-Gatherer has been demonstrated to reduce the complexity of computation in a variety of problems, including such well-known tasks as graph coloring and the well-known transportation problem. It works especially well when the task is decomposable into subtasks with relatively few interactions among them. In the illustrated embodiment, the interactions are concentrated in the area of interest (e.g., the gastrointestinal organ system) and interactions with other organ systems are much less intensive than interactions within the same system. In such embodiments, Hunter-Gatherer provides efficient control of the process.

Figure 3B:
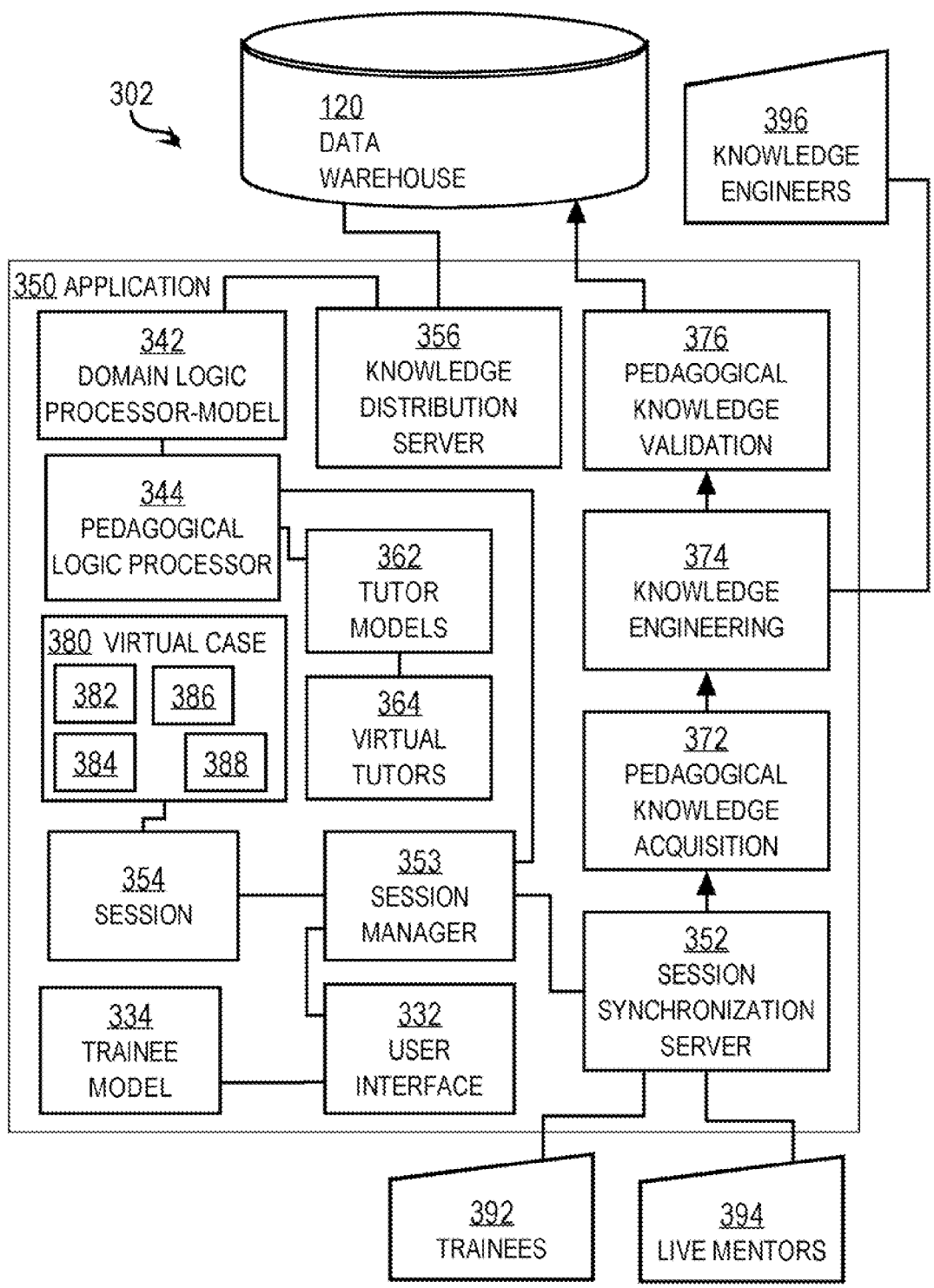
FIG. 3B is a block diagram that illustrates a system with more detailed components of the application, according to an embodiment.

FIG. 3B is a block diagram that illustrates a system 302 with more detailed components of the application, according to an embodiment described next. System 302 includes data warehouse 120 as described above for system 301. System 302 allows for inputs from multiple trainees and live mentors and also allows for input from knowledge engineers on input devices 392, 394, 396, respectively. Although shown as separate input devices for purposes of illustration, in other embodiments one or more trainees, mentors and knowledge engineers share one or more input devices 392, 294, 396.

System 302 includes an application 350 that is an example embodiment of application 150. Application 350 includes a session synchronization server 352, session manager process 353, and session object 354. Application 350 also includes user interface process 332 and trainee model object 334. Application 350 also includes a knowledge distribution server 356, a domain logic processor and model 342, a pedagogical logic processor 344, mentor models 362, and virtual tutors 364 (including virtual tutor 152 depicted in FIG. 1). Application 350 includes a pedagogical knowledge acquisition process 372, a knowledge engineering process 374 and a pedagogical knowledge validation process 378. Application 350 also includes virtual case 380 that involves a single trainee's interactions with a single virtual patient. Any of the objects or processes depicted in application 350 may be performed on any node of a network; it is anticipated that the architecture depicted in FIG. 3B is web enabled in some embodiments.

Session synchronization server 352 is a process that handles multiple simultaneous and delayed interactions with human trainees and mentors through input devices 392, 394. As each trainee signs on to system 302 at terminal 392, the session synchronization server 352 determines whether and which live mentor at terminal 394 is to be associated with the trainee. A session manager process 353 is started to deal with inputs from a particular trainee and zero or more particular associated mentors. Any method known in the art may be used as session synchronization server 352.

The session manager process 353 forms an instance of a session object 354 to store data indicating the results of the session involving the particular trainee and associated mentors. The session object provides links and exchanges data with other objects associated with a virtual case 380, which is described in more detail below.

The user interface process 332 exchanges data with a trainee or live mentor on devices 392, 394 through session manager 353 and session synchronization server 352. The user interface 332 presents interactive elements, such as icons, buttons, data input forms, microphones, speakers and other interactive elements well known in the art to exchange data with a human user. In the example embodiments, the user interface 332 allows the trainee to select a virtual case 380 and to request actions for the virtual case 380, to see feedback from a virtual tutor or live mentor, and to present results from the requested actions. The user interface 332 also allows an associated live mentor to select a virtual case 380, to present status of the virtual case 380, to view a log of trainee actions stored by the virtual case 380, to send messages to the particular trainee, and to assess the performance of the trainee. The live mentor is included as both a fail-safe mechanism and as a way to discover additional mentoring that can be transitioned into the virtual tutor. In some example production embodiments, a synchronous live mentor is not present. In some embodiments, the human mentor steps are implemented as asynchronous interactions.

The options presented to the trainee on device 392 depends on a trainee model object 334 associated with the particular trainee. The trainee model object 334 includes data and functions to generate and respond to the trainee through user interface 332. In some embodiments, a workflow script portion of the trainee model is empty at the beginning of a mentoring session. In other embodiments the system moves a portion of the domain model, such as a virtual normal human, into the trainee model to reflect the system's perception of the trainee's general knowledge and beliefs about the subject matter (i.e., a trainee's "mental model" of the subject matter). The trainee model provides a stepping stone to analysis of basic ontological misconceptions that the trainee may have and to the eventual correction of those misconceptions. While operating the system, the trainee builds up these portions of the trainee model, in the form of choosing a path in a workflow script with branches (furcations). The chosen path includes the component events that the trainee chose during the session, as modified by the mentoring guidance or intervention, or both, if any. It is by comparing this nascent workflow script with the relevant workflow scripts in the mentor model that the system assesses the trainee's progress and provides the necessary mentoring. For example, the trainee's view of the virtual patient, stored in trainee model 334 is compared to the actual virtual patient in the virtual case 380 to assess the trainee's current diagnosis and hence the trainee's performance.

A knowledge distribution server 354 stores and retrieves data on the data warehouse, such as the medical knowledge base 122, mentoring knowledge base 128, normal human data 124, and abnormalities data, and virtual patient data. In example embodiments, the knowledge base includes medical domain and clinical application knowledge.

A domain model is sometimes called an expert model because it represents the material to be studied as encoded by the subject matter experts. The domain can be broad (e.g., all medical practice) or narrow (gastrointestinal systems). The trainee model reflects the trainee's view of the same subject matter and is supposed to get progressively closer to the expert model as learning progresses. The mentor model contains pedagogical knowledge, including knowledge of generic mentor-student interaction. Each of the models can contain different types of knowledge, including three types—declarative (what), procedural (how) and conceptual (why). The three types of knowledge are best captured using different classes of knowledge representation schemata—roughly, semantic networks, production systems and mental models, respectively.

A domain logic processor and model 342 includes a domain model and a domain logic processor. A domain model describes and contains the medical and relevant non-medical knowledge, including relationships between knowledge as well as event scripts defining conditional or non-conditional actions in which the knowledge partakes. The domain logic processor determines the type of case under examination by the particular trainee and, based on the domain model, extracts from the data warehouse 120, through server 356, the appropriate information from the mentoring knowledge base and medical knowledge base. In the example embodiments, the domain model includes domain and workflow scripts. The domain scripts cover, for example, the sequence of events connected with the progression of a disease, with different tracks for the cases when the disease is treated or left untreated. Workflow scripts encode clinical knowledge—the mentors' knowledge about the appropriate diagnostic and treatment procedures. These workflow scripts reflect differences of opinion among experts as well as alternative diagnostic strategies and action sequences.

The pedagogical logic processor 344 is invoked by the virtual tutor to determine and implement the pedagogical approaches for guiding trainee inputs as received from the domain logic processor. In various embodiments, the pedagogical approaches include one or more of (1) leaving the trainee request unmodified for self-discovery; (2) allowing the virtual tutor to modify the trainee request; (3) allowing the virtual tutor to inject addition requests; and (4) allowing the virtual tutor to terminate the trainee's request.

Mentor models 362 are ontological classes that implement one or more of the pedagogical approaches based on user input and trainee history. Virtual tutors 364 (including virtual tutor 152 depicted in FIG. 1 and virtual tutor cognitive agent, described below) are objects that are instances of the mentor model ontological classes.

The pedagogical knowledge acquisition process 372, reviews inputs of live mentors on input device 392 for a current state of the virtual case 380 and determines whether the input follows a protocol already captured in the mentoring knowledge base. If not, the live mentor input and current state of virtual case 380 are forwarded to the knowledge engineering process 374, where they are examined by knowledge engineers operating on I/O device 396. Based on input from knowledge engineers through I/O device 396, a new rule or protocol is determined for responding to trainee requests. The new rule is passed to the pedagogical knowledge validation process 378, which validates the rule. If the rule is validated, then it is added to the mentoring knowledge base 128 in data warehouse 120.

Virtual case 380 includes virtual patient data 382, virtual tools 384, virtual clinicians 386 and session log 388. The virtual patient 382 includes an instance of organism data 310 for a human with at least one abnormality among the ontological objects 316. In some embodiments, the virtual patient also includes a cognitive agent as described in more detail below. In some embodiments, patient 382 is retrieved from the data warehouse 120 through server 356. The virtual tools 384 and virtual clinicians 386 are instances of the ontological classes described above. For example, if the trainee has ordered X-rays, then a virtual tool for X-rays and a virtual radiologist are instantiated as 384, 386, respectively.

The session log 388 records trainee actions, virtual tutor messages if any, live mentor input, if any, and system responses for the particular trainee operating on a particular virtual patient 382. In some embodiments, the session log 388 is stored on data warehouse 120 through server 356.

During steps 240 and 250, one or more of the processes and objects in application 350 are employed. The following describes an example embodiment, after the authoring steps described above.

When the trainee signs on to the system 302 through I/O device 392, the session manager 353 uses the user interface 332 to query the trainee for information that identifies the trainee (a trainee ID). The trainee ID is sent to the pedagogical logic processor 344. The processor 344 sends the trainee ID to the domain logic processor and model 342 which determines an existing virtual case associated with the trainee ID, such as in a previous session by a live mentor. The data for the virtual case 380 is retrieved, for example, from an internal store or from the data warehouse 120. The retrieved virtual case 380 includes the virtual patient 382 and any session logs 388 already accumulated for the case 380. The virtual case 380 is sent to the session manager 352 which instantiates a session object 354 to mange the virtual case 380 during the current session with the particular trainee.

The domain logic processor and model 342 determines the medical knowledge relevant for this virtual patient 382, e.g., gastrointestinal systems medical knowledge for use by one or more virtual tutors. In the example embodiments the domain logic processor and model 342 also determines the pedagogical approach to use with the particular trainee and case. The system loads the ontological classes for mentor models 362 that implement the determined pedagogical approach from the mentoring knowledge base 128 in data warehouse 120 and replicates that approach for several medical areas (e.g., pulmonary and gastrointestinal) for several mentor models. The mentoring knowledge base 128 includes any mentoring protocols validated during previous sessions. One or more virtual tutors 364 are later instantiated from the mentor models 362 as needed to respond to user requests.

In step 240 a trainee requests an action, whether investigative or interventional, using one or more virtual tools accessible through user interface 332 presented on I/O device 392 by session manager 353 through server 352.

During step 252, the session manager 353 sends the request to the pedagogical logic processor to determine whether to allow or modify the requested action. The processor 344 makes the determination by instantiating one of the mentor models 362 as a virtual tutor 364 and sending the request to the virtual tutor 364. The virtual tutor 364 sends a response to the processor 344. In some embodiments, during step 254, the pedagogical processor 344 sends the request and virtual tutor response through session manager 353 to the live mentor at I/O device 394, if any, using the user interface 332. If the live mentor provides a response, the response is sent to session manager 353. The session manager 353 then forwards the trainee request and either the virtual tutor response or the live mentor response, or both, to the session object 354. The session object stores the request and mentor responses in the log 388. The live mentor response, if any, is also forwarded by the session synchronization server 352 to the pedagogical knowledge acquisition process 372 for processing as described above.

The session object 354 includes functions that create an instance of a virtual tool 384 and virtual clinician 386 to implement the trainee request, as modified by the live or virtual tutors. The virtual clinician 386 retrieves data from the virtual patient 382. If directed by the request, the virtual clinician 386 changes the virtual patient 382, e.g., by deleting an abnormal object that is surgically removed. The virtual clinician 386 then forms a response which is sent to the session object 354, which records the response in the log 388.

In step 280 the response is sent to the trainee at I/O device 392 by the session object 354 through the session manager 353 and session synchronization server 352.

In step 258, the session object 354 updates the virtual patient 382, e.g., by advancing events on one or more normal or abnormal objects in time and recalculating the data values for the parameters of the objects included in the patient 382. In some embodiments, the session object 354 sends another response message based on the recalculated virtual patient, e.g., a status report on the patient at the next elapsed time. The message is recorded in the log 388.

During step 280, the message, e.g., the status report, is sent by the session object 354 to the trainee at I/O device 392. During step 290 the message, e.g., the status report, is sent to the live mentor at I/O device 394, if any.

During step 250 the message, e.g., the status report, is sent to the virtual tutor 364. In an example embodiment, the live mentor at device 294 sends a live feedback message to the virtual tutor 364 during step 254. Based on the message to the virtual tutor 364 and the pedagogical processor and the live mentor, if any, the virtual tutor 364 sends a mentor feedback message to the session manager 353. The session manager 353 forwards the mentor feedback message to the session object 354, which records the mentor feedback message in log 388.

During step 280, the session manager 353 forwards the mentor feedback message to the trainee at I/O device 392.

The example embodiments provide multiple advantages over prior art approaches. In the example embodiments, the patient data sets are rich in detail and knowledge, and evolve as new ontological classes are added. In some embodiments, the patient data sets are standardized, such as in the format of the national Library of Medicine (NLM), for ease in transferring between systems. Actual data from a patient with the disease of interest can be inserted into an instance of a virtual patient, making the simulation even more realistic. The ontological classes and objects, polymesh data and image data based on the actual disease data can be used to create a databank of standardized diseased patient data in a sharable form for other applications, just as image databanks are available today. The Joint Photographic Experts Group (JPEG) and the picture archiving and communications system (PACS) formats for imagery data are fairly standard and thus are readily shared. The human data formats provide a natural connection to other cognitive simulators that are later developed as certain part-task simulators. As automated image interpretation evolves (e.g., for CT scans), a real image can be imported, used to generate polymeshes and links to ontological objects, and presented for interpretation by the trainee, without involvement by a human author. This will make an additional component of the system 301 automatic. The ontological classes, polymesh data and image data used herein can serve as a defacto standard for the "patient sharable object" for the medical care industry.

4. Virtual Persons with Cognitive Agent

According to an embodiment of the invention, the virtual patient is implemented with two agents; a physiological agent and a cognitive agent. The physiological agent includes data in working memory and processes in an engine for a simulator that causes the physical properties of the virtual patient to be determined and advanced in time and in response to intervention.

The cognitive agent includes data in memory and processes in multiple engines, including a planner engine and a natural language processor engine. The cognitive agent accounts for the susceptibility of a virtual patient to pain and symptoms that affects the timing of the patient's first appearance before a doctor, and therefore the state of the disease at their first encounter. In some embodiments, the cognitive agent also accounts for the ability of the patient to verbally convey their symptoms based on age, education, culture, belief system or other factors, or some combination. In some embodiments the other factors include truthfulness of the virtual patient, level of hypochondria, level of compliance, nature of memory (how well and accurately things are remembered over time), among many others, in any combination. Thus, the cognitive agent can fabricate symptoms, mislead, and otherwise modify the data presented to the trainee.

Figure 5A:
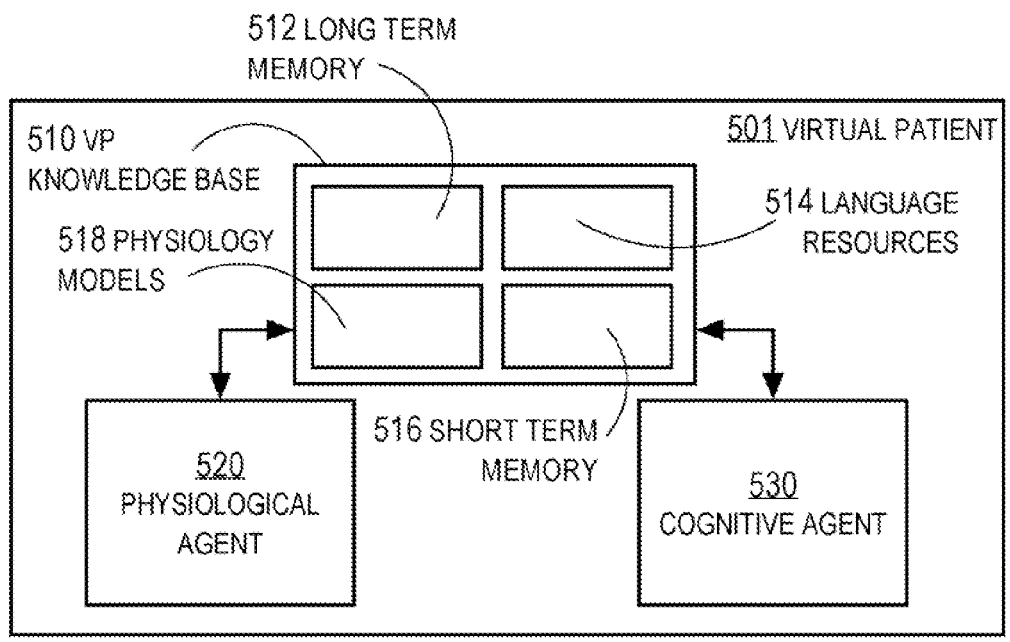
FIG. 5A is a block diagram that illustrates components of a virtual patient, according to an embodiment.

FIG. 5A is a block diagram that illustrates components of a virtual patient 501, according to an embodiment. In the illustrated embodiment, the virtual patient 501 includes a virtual patient knowledge base data structure 510, a physiological agent 520 and a cognitive agent 530. The knowledge base 510 includes long term memory data structures 512, language resources data structures 514, short term memory data structures 516 and physiological models data structures 518. Because the language resources data structures 514 are included, the illustrated embodiment is capable of natural language processing for interpreting input and for generating output at the virtual patient.

Although data structures 510, 512, 514, 516, 518 in FIG. 5A (and others in subsequent block diagrams) are shown as single blocks of contiguous data within a single block for purposes of illustration, in other embodiments, one or more data structures are broken up into two or more data structures on one or more different blocks on one or more different devices, such network storage appliances.

In the illustrated embodiment, the data in knowledge base data structure 510 is a collection of concepts including objects and event scripts in the OntoSem schema. The physiological agent 520 and cognitive agent 530 are sets of processes that manage data in the knowledge base 510 in response to input and output from other components of the system (e.g., system 302).

Again, although the physiological agent 520 and the cognitive agent 530 in FIG. 5A (and others in subsequent block diagrams) are shown as single blocks, in other embodiments each agent is composed or two or more processes executing on the same or different processors on the same or different device in series or in parallel.

A physiological component includes the physiological agent 520 and supporting data in the virtual patient knowledge base data structures 510. A cognitive component includes the cognitive agent 530 and supporting data in the virtual patient knowledge base data structures 510. It is anticipated that some data items in the virtual patient knowledge base data structure 510 belong to both the physiological component and the cognitive component.

Similarly, in some embodiments, the virtual tutor is implemented with a cognitive agent. The tutor cognitive agent includes data in memory and processes in multiple engines, including a planner engine and a natural language processor engine. In the illustrated embodiment, the cognitive agent accounts for the pedagogical model being implemented, previous dialog with the trainee, and the particular language used to interact with the trainee, among other factors.

Figure 5B:
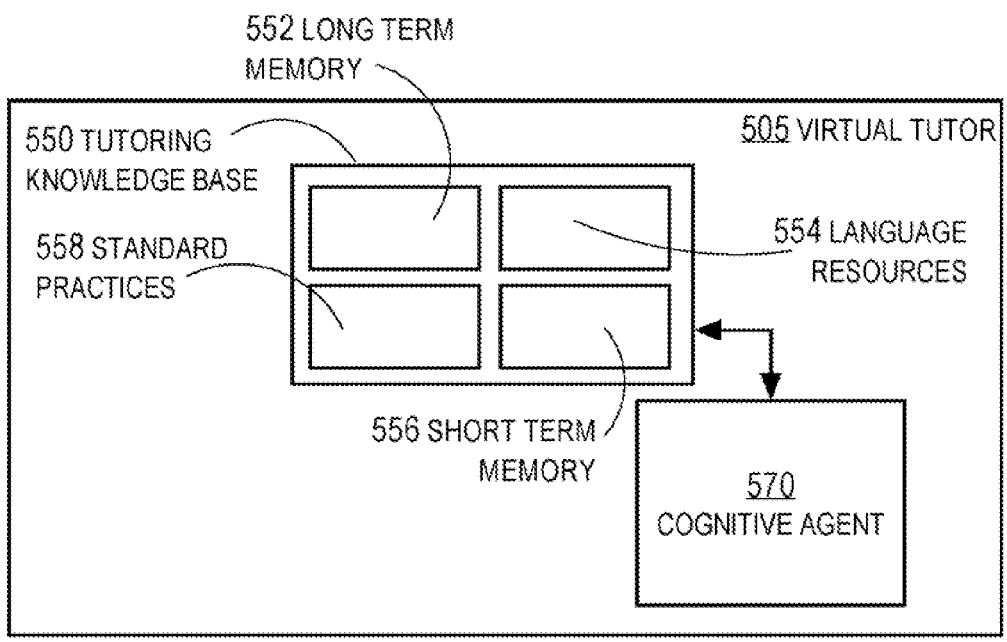
FIG. 5B is a block diagram that illustrates components of a virtual tutor, according to an embodiment.

FIG. 5B is a block diagram that illustrates components of a virtual tutor 505, according to an embodiment. In the illustrated embodiment, the virtual tutor 505 includes a tutor knowledge base data structure 550, and a cognitive agent 570. The tutor knowledge base 550 includes long term memory data structures 552, language resources data structures 554, short term memory data structures 556 and standard practices data structures 558. Because the language resources data structures 554 are included, the illustrated embodiment is capable of natural language processing for interpreting input and for generating output at the virtual tutor.

In the illustrated embodiment, the data in tutor knowledge base data structure 550 is a collection of concepts including objects and event scripts in the OntoSem schema. The cognitive agent 570 is a set of processes that manages data in the tutor knowledge base 550 in response to input and output from other components of the system (e.g., system 302).

Figure 6:
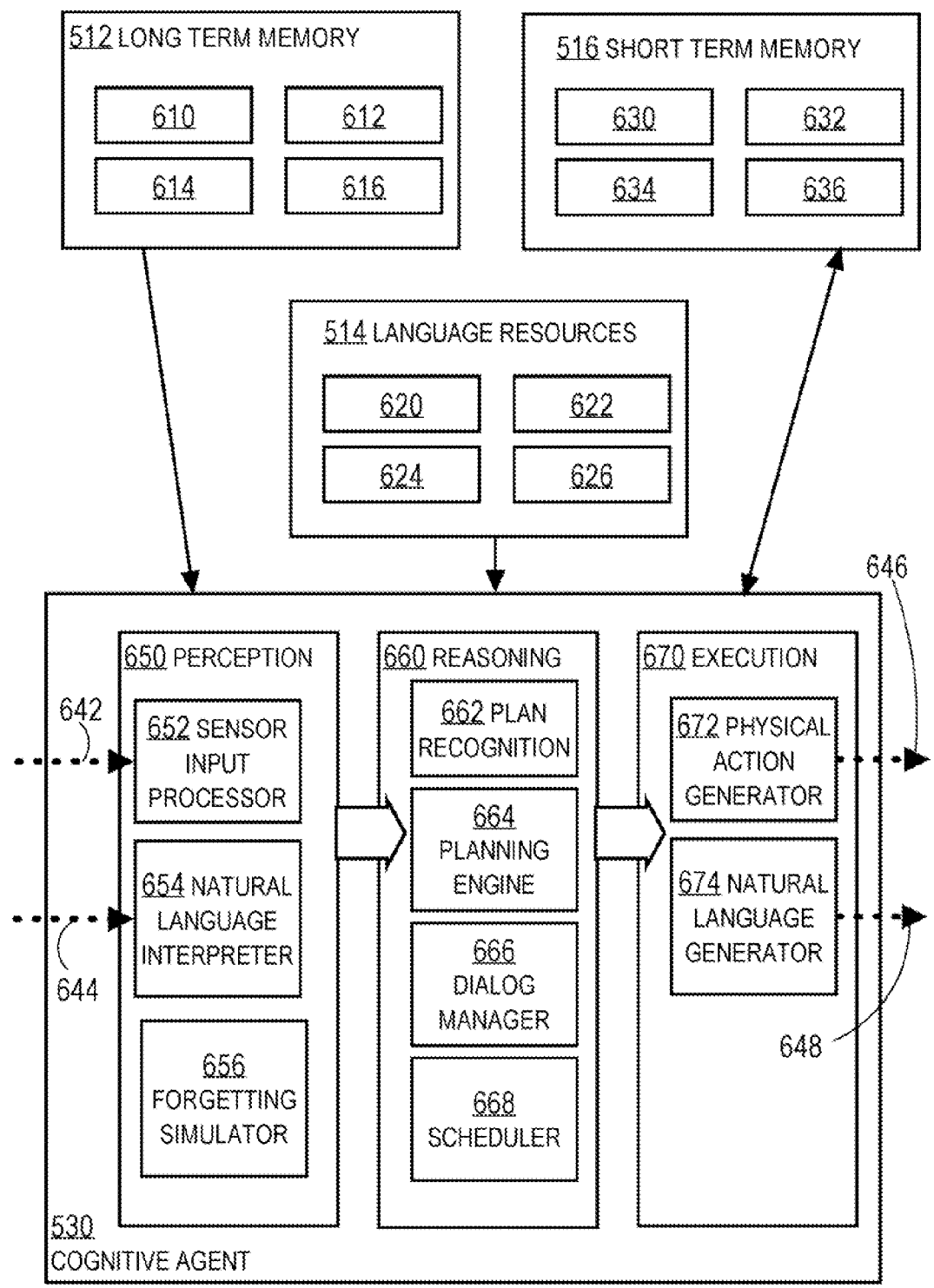
FIG. 6 is a block diagram that illustrates components of a virtual patient cognitive agent and associated knowledge base components, according to an embodiment.

FIG. 6 is a block diagram that illustrates a virtual patient cognitive component including a cognitive agent 530 and associated knowledge base data structures, according to an embodiment. The cognitive agent 530 includes perception processes 650, reasoning processes 660, and execution processes 670. Data for these processes are received from long term memory, short term memory and language resources data structures 512, 516 and 514, respectively.

The long term memory data structure 512 includes structures for data over which a particular virtual patient retains command. Some of the values in this data structure are originally set for all virtual patients and other values are set when the virtual patient is instantiated. For example, in the illustrated embodiment, the long term memory data structure 512 includes objects and event types data structures 610, memory of past events data structures 612, goal and plan types data structures 614, and rules of reasoning data structures 616. The objects and event types data structures 610 hold data that indicates the categories of objects and events of which the virtual patient has awareness, such as characteristics of symptoms and families and employment and sustenance. The memory of past events data structures 612 hold data that indicates the timing and values of specific event instances, such as swallowing pain beginning a week earlier, and death of parent three years earlier from lung cancer. The goal and plan types data structures 614 hold data that indicates the characteristics of different goals, such as obtaining a cure, reducing pain, minimizing expenses, and plan types that advance those goals, such as getting and following best medical advice, obtaining drugs that reduce pain, acknowledging ailments that are covered by health insurance. The rules of reasoning data structures 616 hold data that indicates the reasoning rules, such as rules for selecting, triggering and advancing specific scripts and plans and posting effects of events.

The short term memory data structure 516 includes structures for data which is current or recently learned or generated by the particular virtual patient. Many of the values in this data structure are originally set when the virtual patient is instantiated. For example, in the illustrated embodiment, the short term memory data structure 516 includes active objects and events data structures 630, recent dialog history data structures 632, active goals and plans data structures 634, and scheduling agenda data structures 636. The active objects and events data structures 630 hold data that indicates the current values of objects and events, such as it does not hurt to swallow at the moment, the patient is 60 years and 7 months old, she experiences regurgitation several times a day, food has been ingested two hours earlier, and the patient is retired. The recent dialog history data structures 632 hold data that indicates the understood content and sequence of the conversation exchanged between the patient and the trainee and the virtual tutor. The active goals and plans data structures 634 hold data that indicates the currently active set of goals and their corresponding plans, such as the goal to minimize expense and the plan to find out what insurance covers and try that treatment first. The scheduling agenda data structures 636 hold data that indicates a relative importance of current goals, plans, plan steps, objects and events in the patient's belief system, e.g., present pain is more important than past pain and pain reduction is more important than cure.

The language resources data structure 514 includes structures for data related to converting between words and concepts such as objects and events in the ontology. For example, in the illustrated embodiment, the language resources data structure 514 includes lexicon data structures 620, discourse and dialog model data structures 622, ecology, morphology, syntax data structures 624, and semantic microtheories data structures 626. The lexicon data structures 620 hold data that associates concepts in the ontology with particular words or phrases in the particular language or dialect of the particular virtual patient. The discourse and dialog model data structures 622 hold data that indicates goals, plans and preferences with respect to communication with other agents, appropriate conceptual responses to particular concepts presented by another speaker in the culture of the particular patient, such as a reluctance to appear to agree or a reluctance to appear to disagree. The ecology, morphology, syntax data structures 624 hold data that supports the ability of the cognitive agent to understand orthographic peculiarities, proper names, abbreviations, word forms (e.g., plural or singular) as well as syntactic properties present in the natural language locutions. The semantic microtheories data structures 626 hold data that indicates specific transformations between words and concepts, such as transformations involving time, quantification, approximation, issues relating to sets and ordered lists, and several different aspects of reference and its resolution.

The cognitive agent 530 responds to sensor input data 642 and verbal input data 644, retrieves information form the data structures described above, and outputs a response that includes an update to the short term memory data structures 516, physical action data 646 and verbal output data 648. The sensor input data 642 indicates non-verbal phenomena perceived by the virtual patient, such as brightness in the room, touching by the trainee, an injection by a virtual agent, and an object presented to the virtual patient, such as food or a pill and glass of water. The physical action data 646 indicates an action performed by the virtual patient, such as leaving the interview, eating the food, taking the pill and the timing. The verbal input data 644 and verbal output data 648 indicate information given to the virtual patient and information received from the virtual patient, respectively. The verbal input data 642 includes verbal input provided by the trainee, the virtual tutor and the live mentor, in any combination. In some embodiments, the verbal input data 644 and verbal output data are selected from a limited set of canned phrases with predefined precise meanings. However, in the illustrated embodiment, the verbal input data 644 or verbal output data 648, or both, are natural language expressions, either typed as characters, or transmitted audibly.

The perception processes 650 include a sensor input processor 652, a natural language interpreter 654, and a forgetting simulator 656. The sensor input processor 652 receives the sensor input data 642, converts it to a form used in the short term memory data structures 516 or the reasoning processes 660, or both, and forwards the converted data. The natural language interpreter 654 converts the verbal input 644 to values for one or more concepts such as objects and events in the domain knowledge base. In embodiments that use predefined phrases, the natural language interpreter 654 is omitted. The forgetting simulator 656 reduces the data in one or more short term memory data structures 516, such as the active objects and events data structures 630, active goals and plans data structures 634 and the dialog history data structures 632 to simulate memory lapses that occur in real patients. In some embodiments, the forgetting simulator 656 is omitted.

The reasoning processes 660 include a plan recognition process 662, a planning engine 664, a dialog manager 666, and a scheduler 668, in the illustrated embodiment. The cognitive agent 530 is goal driven and knows a set of plans for attaining a goal from the active goals and plans data structures 634 in the short term memory data structure 516. The plan recognition process 662 recognizes the current plans and changes in plans of other agents, as communicated through language or action. The scheduler 668 prioritizes plans and event scripts based on the data in the scheduling agenda data structure 636 in the short term memory data structure 516; and advances them in time using the planning engine. The planning engine 664 selects a plan to execute from a set of active plans and advances this plan by executing a step in the plan and subsequently determining whether the plan step succeeds or fails. The dialog manager 666 places a conceptual verbal response in the context of the dialog history in data structure 632 in short term memory data structure 516 and stores that response in the dialog history data structure 632 in short term memory data structure so that this response can be taken into account when the cognitive agent selects and executes its own discourse plan that results in the production of a natural language locution The execution processes 670 include a physical action generator 672 and a natural language generator 674. The physical action generator 672 converts the conceptual response from the planning engine to the action output data 646. The natural language generator 674 converts the verbal concepts determined by the dialog manager 666 to verbal output 648 that uses natural language expressions. In embodiments that use predefined phrases, the natural language generator 674 is omitted.

Figure 7:
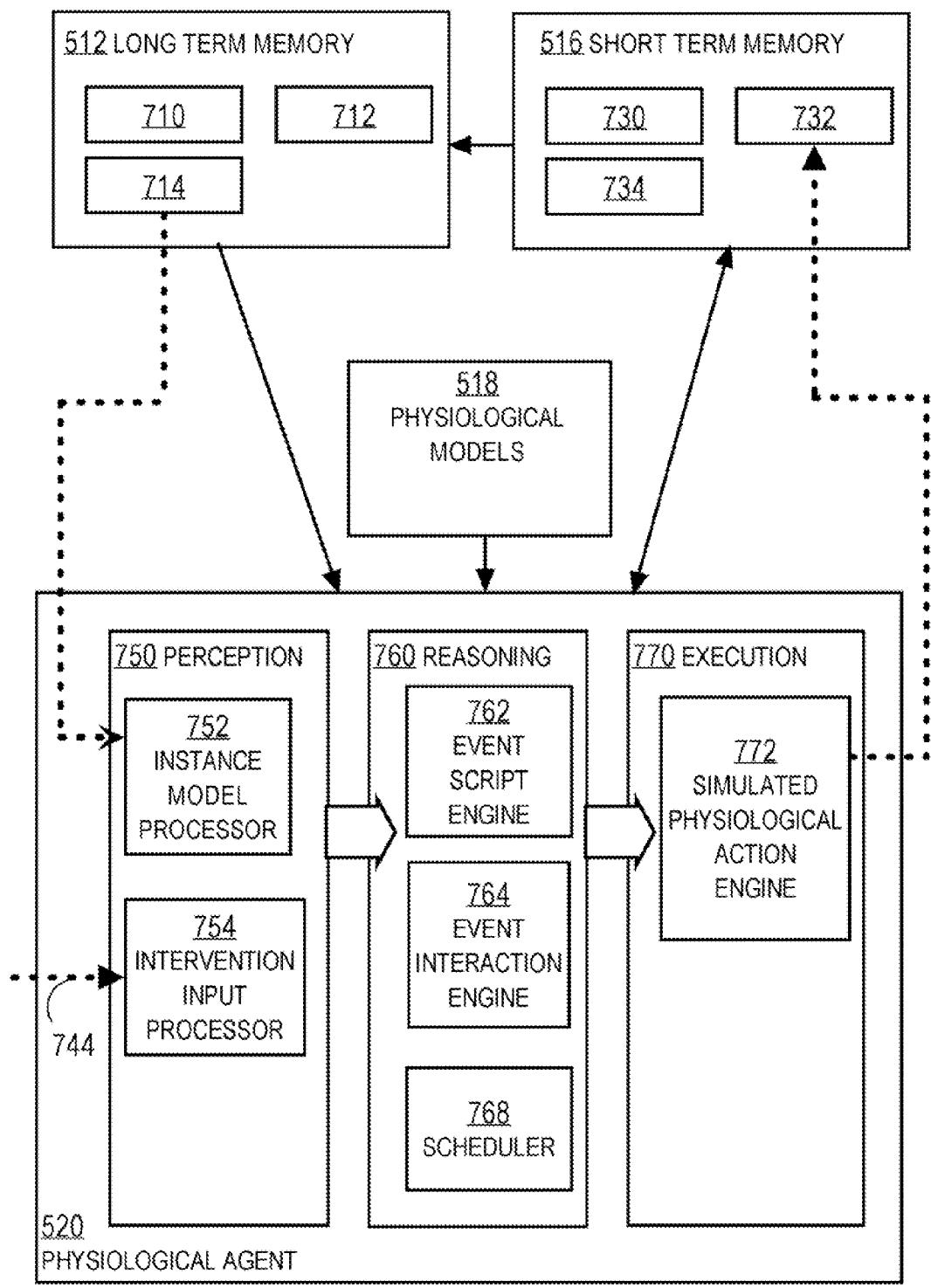
FIG. 7 is a block diagram that illustrates components of a physiological agent and associated knowledge base components, according to an embodiment.

FIG. 7 is a block diagram that illustrates a physiological component that includes a physiological agent 520 and associated knowledge base components, according to an embodiment. The physiological agent 520 includes perception processes 750, reasoning processes 760 and execution processes 770. Data for these processes are received from long term memory, short term memory and physiological models data structures 512, 516 and 518, respectively.

The long term memory data structure 512 includes structures for data which persist for the particular virtual patient (VP) until final diagnosis. For example, in the illustrated embodiment, the long term memory data structure 512 includes rules of reasoning data structures 710, history of past VP states data structures 712, and VP instance model 714. The rules of reasoning data structures 710 hold data that indicates the reasoning rules, such as logic rules for triggering specific events, for establishing preferences among active goals and plans, for establishing the times of instantiating sub-events in event scripts, for disambiguating natural language inputs with the aim of extracting their meaning, etc. The history of past VP states data structures 712 hold data that indicates time of changes to the VP instance and records those changes. The VP instance model 714 hold data that describes the virtual patient instance, such as the organism data 310 for the particular VP.

The short term memory data structure 516 includes structures for data which is current or recently modified in the particular virtual patient. Many of the values in this data structure are originally set when the virtual patient is instantiated. For example, in the illustrated embodiment, the short term memory data structure 516 includes active objects and events data structures 730, current VP state data structures 732, and action scheduling agenda data structures 734. The active objects and events data structures 730 hold data that indicates the current values of objects and events, such as a current phase of the complex swallowing event, described in more detail below. The current VP state data structures 732 hold data that indicates the deviations from the initial instance, for example, current values of organism data, such as the new location and properties of a growing tumor. The action scheduling agenda data structures 734 hold data that indicates a relative importance of current objects and events in the virtual patient, such as completing the swallowing event occurs before increasing tumor size.

The physiological models data structure 518 includes structures for data related to physiological processes, such as relevant event scripts (like swallowing event, digestion of swallowed food event), relation of tumor size to nausea, among others. In some embodiments, the physiological models data structure includes the VP instance model 714.

The physiological agent 520 responds to the VP instance model 714 and medical intervention data 744, retrieves information from the data structures described above, and outputs a response that includes an update to the current VP state data structure 732 in the short term memory data structures 516. The medical intervention data 744 indicates an event that changes the tissues of the virtual patient, such as injection of therapeutic or diagnostic substances or devices or removal of tissue.

The perception processes 750 include an instance model processor 752 and an intervention input processor 754. The intervention input processor 754 receives an identity of an event from a virtual agent (such as a virtual surgeon or virtual radiologist) and determines the portion of the VP instance model that is relevant. The instance model processor 752 receives data from the virtual patient instance model, such as the next time to advance various events in the VP instance model and forwards the relevant information. The perception processes 750 also model the conscious perception of the VP (embodied in its cognitive agent component) of the physiological and physical events that caused perceivable changes in VP's physiology or anatomy.

The reasoning processes 760 include an event script engine 762, an event interaction engine 664, and a scheduler 768, in the illustrated embodiment. The scheduler 768 prioritizes event scripts based on the data in the action scheduling agenda data structure 734 in the short term memory data structure 516 and data output by the instance model processor 752; and advances them in time using the event script engine. The event script engine 762 advances a particular event script, such as swallowing a radiological contrast substance. The event scripts include automatic changes in time frames between sequenced sub-events. Thus, a chronic disease that has some events spaced months apart has an acute flare-up sub-event with changes from minute-to-minute. The script engine automatically accommodates these changes in time scales. The event interaction engine 664 determines whether the advancement of one event initiates, facilitates, terminates or otherwise affects the advancement of another event script, and schedules the modification of the affected event.

The execution processes 770 include a simulated physiological action engine 772 which changes the current VP state data structure 732 based on the event scripts advanced by the reasoning processes 760.

Figure 8:
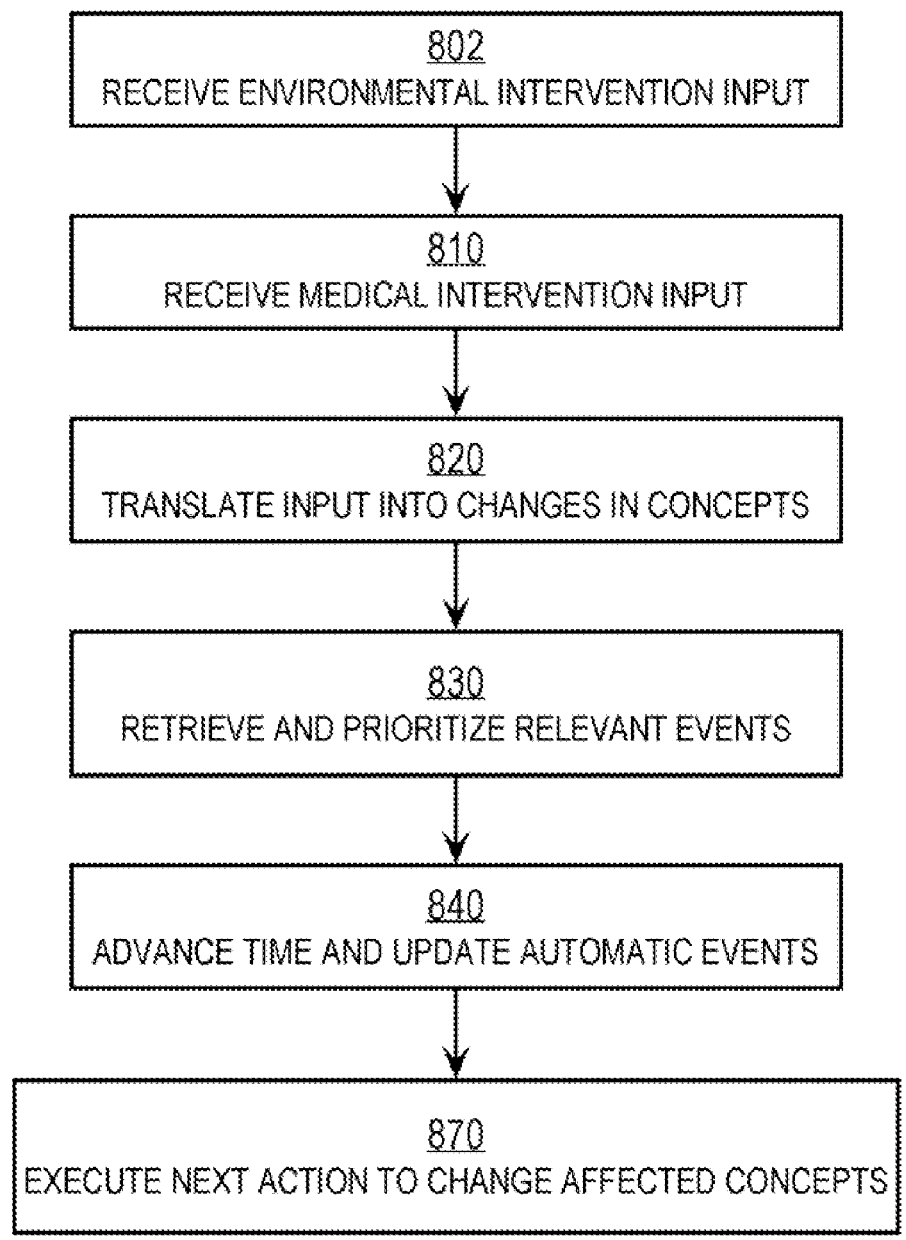
FIG. 8 is a flow diagram that illustrates at a high level a method for a virtual patient physiological agent, according to an embodiment.

FIG. 8 is a flow diagram that illustrates at a high level a method 800 for a virtual patient physiological agent, according to an embodiment. In step 802 environmental intervention input is received. For example, data indicating the passage of time, exposure to toxins and stress, among others, is received from the VP instance model by instance model processor 752. In step 810, medical intervention input is received, e.g., input 744 is received by intervention input processor 754.

In step 820, input is translated into changes in one or more concepts. For example, input is converted into concepts used for one or more event scripts by instance model processor 752 and by intervention input processor 754 and passed to one or more reasoning processes 760 and short term memory structures 516, such as active objects and events data structures 730 and action scheduling agenda data structures 734.

In step 830, relevant event scripts are retrieved from the VP knowledge base and prioritized. For example, scheduler 768 obtains active events from data structure 730 in short term memory structure 516 and prioritizes them based on action scheduling agenda data in data structure 734 in short term memory structure 516.

In step 840, time is advanced based on the input and active events are automatically updated. For example, event script engine 762 operates on the events scheduled by the scheduler 768. Events that interact with other events cause the event interaction engine 764 to create or retrieve and then advance the interacting events during step 840.

In step 870, the changes wrought by the advanced events are executed as an action to change affected concepts. For example, the new values for one or more concepts are passed to the simulated physiological action engine 772, which updates the current VP state data structure 732 in short term memory data structure 516.

FIG. 9 is a flow diagram that illustrates at a high level a method 900 for a virtual patient cognitive agent, according to an embodiment. In step 902 some data in memory data structures 516 and 512 is reduced. For example, forgetting simulator 646 erases some data to simulate virtual patient forgetfulness. In step 912, simulated sensor input data is received. For example, data indicating the passage of time, exposure to touch, heat and cold, odors, tastes, light and noise, among others, is received by sensor input processor 642. In step 914, verbal instructions and questions from the trainee are received, e.g., input 644 is received by natural language interpreter 654.

In step 920, input is translated into changes in one or more concepts. For example, input is converted into concepts used for one or more plans and event scripts by sensor input processor 652 and by natural language interpreter 654 and passed to one or more reasoning processes 660 and used to update short term memory structures 516, such as active objects and events data structures 730, dialog history 632, active goals and plans data structures 634 and scheduling agenda data structures 636.

In step 930, relevant goal and plan scripts are retrieved from the VP knowledge base. For example, the plan recognition process 662 retrieves the active goals and plans from the data structures 634 in the short term memory data structure 516. In step 932 relevant event scripts are retrieved from the VP knowledge base. For example, the scheduler process 668 retrieves the relevant active objects and events from the data structures 630 in the short term memory data structure 516. In step 934 the plans and events are prioritized. For example, scheduler 668 prioritizes them based on scheduling agenda data in data structure 636 in short term memory structure 516.

In step 940, time is advanced based on the input; and active events are automatically updated. For example, an event script engine operates on the events scheduled by the scheduler 668.

In step 950, the plan is advanced or changed based on the input and updated events and objects. For example, the planning engine 664 operates on the plans scheduled by the scheduler 668, and determines whether the plan is succeeding or should be changed or whether the goal should be changed. Depending on the decision, the next step of the current plan or the first step of a new plan is determined and the active goals and plans are updated in data structures 634.

In step 960, the next statement and actions according to the updated plan is output to the execution processes 670. If the plan calls for a statement, step 960 includes employing the dialog manager 666 to put the next statement in the contest of the dialog history stored in data structures 632 in short term memory data structures 516.

In step 970, the actions or statements produced by the advanced events and plans are executed as an action to change affected concepts. For example, the new values for one or more concepts is passed to the physical action generator 672, which causes the VP to take an action by filling a value in a concept that describes the VP actions. When the plan calls for a verbal expression from the virtual patient, such as answer to a query from the trainee, in some embodiments, step 970 includes employing changing a concept for the statement into a natural language expression using the natural language generator 674 and the language resources in data structures 514.

FIG. 10 is a flow diagram that illustrates at a high level a method 1000 for a virtual tutor cognitive agent 570, according to an embodiment. In step 1014, verbal suggestions and questions from the trainee are received.

In step 1020, input is translated into one or more concepts. For example, input is converted into concepts by a natural language interpreter and those concepts are passed to one or more reasoning processes in agent 570 and to one or more short term memory structures 556.

In step 1030, relevant standard practices are retrieved from the VP knowledge base standard practices data structures 558. In step 1032 relevant event scripts and past dialog between the tutor and virtual patient are retrieved from the VP knowledge base. For example, a scheduler process identifies and retrieves the relevant virtual patient dialog from the short term memory data structure 516 and retrieves active objects and events for the tutor from the short term memory data structure 556.

In step 1040, time is advanced based on the input; and active events are automatically updated. For example, an event script engine operates on the events scheduled by a scheduler.

In step 1050, the virtual tutor cognitive agent 570 determines whether a trainee suggestion is appropriate based on inputs and events and dialog and standard practices. For example, based on reasoning in the long term memory data structures 552, a reasoning process in the tutor cognitive agent 570 determines whether the trainee suggestion is adequate.

In step 1060, the next statement is generated and output to the execution processes. For example, based on reasoning in the long term memory data structures 552 and a pedagogical model in the short term memory data structures 556, a reasoning process in the tutor cognitive agent 570 determines a conceptual statement to send in response to the trainee suggestion.

In step 1070, the statements produced by reasoning processes are executed as an action to change affected concepts. In some embodiments, step 1070 includes changing a concept for the statement into a natural language expression using a natural language generator and the language resources in data structures 554.

5. Example Use of Natural Language Constructs for Medical Data

According to some embodiments of the invention, medical knowledge is stored and processed in the training system, including the virtual patient, using the same constructs and processes (e.g., the same structures) as are also used for natural language processing, e.g., using Ontological Semantics. For example, high-level, language-independent concepts are defined with several attributes or properties. Specific instances of the concept are formed by specifying values for the attributes. Some concepts can include scripts to represent events that can be nested to form more complex events from more simple events Plans are also implemented as scripts. A lexicon and other language resources are used to translate between instances of a concept and a natural language expression in a particular language.

The use of the same knowledge structures are as used for language processing to model medical systems has the advantage of using existing methods to handle the new information, and also supporting a natural language human interface between the knowledge base and the user, including authors, trainees and live mentors.

The use of Ontological Semantics to model example medical systems and disease progression is described in more detail here.

5.1 Has-Event-as-Part

The system elicits and records knowledge about basic physiological processes as event scripts recorded in the HAS-EVENT-AS-PART slot of EVENTS in the OntoSem ontology. Take, for example, a SWALLOW script, which is related to the modeling of diseases of the esophagus. It has two subevents, the OROPHARYNGEAL-PHASE-OF-SWALLOWING and the ESOPHAGEAL-PHASE-OF-SWALLOWING, each of which has its own subevents, which have their own subevents, and so on, as desired.

Consider the top level of the ESOPHAGEAL-PHASE-OF-SWALLOWING, written in Lisp-compatible format:

```
(esophageal-phase-of-swallowing
    (props
        (segment-list C6-SEGMENT-OF-ESOPHAGUS ...
            T10-SEGMENT-OF-ESOPHAGUS));
        the list actually contains 10 elements
    (has-event-as-part
        (value peristalsis:from_larynx)
        (value contract-muscle:crico)
        (value
            (do ((i 1 (+ i 1))
            (segment1 (get-element segment-list i)
                (get-element segment-list i))
            (segment2 (get-element segment-list (+ i 1))
                (get-element segment-list (+ i 1))))
                (peristalsis:R (source segment1)
                    (destination segment2))
                until (= i 9))
        (value peristalsis:to_stomach)))
```

This says that this phase of swallowing has four immediate subevents, descriptively named by the variables peristalsis:from_larynx, contract-muscle:crico (i.e., cricopharyngeus), peristalsis:R (R implies 'regular'), and peristalsis:to_stomach.

The third event, peristalsis:R, is actually a loop that moves the bolus (chewed food) through the esophageal segments that comprise the body of the esophagus. The list of segments (C6, C7 followed by T1-T10) is written in the props field of the event that calls the loop. The top-level event in the loop, peristalsis:R, actually has many subevents, which underscores the savings achieved by incorporating such a control structure.

In addition to basic events and loops, the objects that fill the HAS-EVENT-AS-PART slot can be conditionals.

Each subevent is "expanded" into a frame that includes all relevant properties and values: for example, the swallower is an experiencer of all of the stages of peristalsis, the bolus (swallowed food) is the theme, each subevent has a duration, some have effects represented as changes in property values, among others.

Describing basic physiology in terms of events and their parts is convenient for knowledge elicitation because knowledge engineers (e.g., medical knowledge authors) can query subject matter experts (SMEs) in terms of what happens first . . . and next . . . and after that . . . . Moreover, any of the subevents can be expanded or left as a stub at any point, depending not only upon the priorities of SMEs at a given time, but also upon what medical knowledge is currently available. Viewing this effort in the long term, the ability to easily replace stubs (acting as "bridges") by newly understood physiological processes is valuable.

As concerns implementation, event-oriented scripts of the type just described offer an alternative to object orientation in programming and knowledge management. A mixed model is used in the illustrated embodiments, such that object- or event-orientation is used as best fits a given knowledge encoding need.

5.2 Table-Off-a-Timeline

Apart from basic physiological scripts, the system also uses knowledge about diseases, their signs and symptoms, diagnostics and treatments. While all of these could be thought of as scripts of the type just discussed, an object-oriented metaphor was found to be more useful, both in terms of knowledge elicitation/encoding and in terms of processing for some classes of diseases.

The metaphor developed for some diseases is a table dangling off a timeline, whose skeleton looks as depicted in Table 1. This metaphor works better for some classes of diseases than for others.

TABLE 1

Example Disease Model.

| | time: | | | | |
|---|---|---|---|---|---|
| | t0 | t1 | t2 | t3 | t4 |
| physiological properties and values | | | | | |
| symptoms | | | | | |
| diagnostics | | | | | |
| treatments | | | | | |

The variables t0 to t4 represent points in time during the progression of the disease. A given number of t values is set for each disease and represents the typical number of stages of the disease as conceptualized by physicians. However, physician-authors of instances of VPs set the values for these variables in order to generate different speeds of disease progression. In an example embodiment, the diagnostic rows and treatment rows are omitted.

Physiology. The physiology section is actually a block of rows that represent different properties of the VP whose values change over time in coordinated ways due to the effects of the disease. Take, for example, the esophageal disease achalasia, which progressively renders a patient unable to swallow due to loss of relaxing neurons in the lower esophageal sphincter (LES) and subsequent failure of the LES to relax and let food pass. The ratio of contracting to relaxing neurons in the LES is the independent variable, and it decreases over time in what is modeled as a linear progression between t-stages. Property values that are dependent upon this ratio include the basic LES pressure, relaxed LES pressure, the diameter of the lower esophagus, and many others, which change in corresponding, predictable ways over time.

Symptoms. Symptoms are a notoriously variable phenomenon in human physiology. Under the same physiological conditions, some patients will experience a symptom and some will not. Moreover, the same patient may experience a symptom one day and not another day despite apparently identical stimuli. Therefore, flexibility in the relationship between physiology and symptoms is necessary to support realistic simulation.

For purposes of a training-oriented simulation (which does not require building a precise and comprehensive physiological model), there are two types of symptoms that are recorded in different ways. First, there are symptoms that are associated with a given event and may or may not be associated with a particular disease. For example, symptoms recorded in the SWALLOW script include but are not limited to difficulty swallowing due to a physical blockage in the lumen of the esophagus, and pain upon swallowing because the swallowed substance either is very acidic or is mildly acidic but passes through an already irritated esophageal segment. These symptoms occur to any virtual human during any occurrence of SWALLOW when the given preconditions or combinations thereof obtain. Since real humans—and, by extension, VPs—swallow many times a minute, there is much opportunity for event-driven symptoms in the VP.

The second type of symptom is one brought upon by a disease itself—or, more specifically, by the changes in physiological property values that it causes. Such symptoms are recorded with reference to the same time values as the associated disease. For example, an achalasia patient might experience difficulty swallowing or weight loss with varying intensities over the course of the disease. The expected intensities of such symptoms are recorded in the disease script as ranges, from which VP authors select a particular value for each VP at each time. In some embodiments, the system selects defaults. In some embodiments, values for different stages are calculated by the simulator based on some general VP property value, like "sensitivity to discomfort" or "hypochondria level.". Symptom tables like this one reflect clinical rather than purely physiological knowledge, since the physiology of a disease like achalasia, and the relationship between it and patient symptoms, are not sufficiently documented to permit a lockstep correlation. The change in intensity of symptoms from one time to the next is understood as a linear function, just as with the progression of the disease itself. So if the author of a VP decides that his/her patient will have pain on swallowing at an intensity of 0.1 (on the abstract scale {0,1}) at t2, and at an intensity of 0.3 at t3, then the simulator calculates any intermediate values necessary should a trainee request diagnostic procedures at a time between t2 and t3.

The blocks describing disease physiology and patient symptoms are directly used for the simulation. The other two blocks—devoted to diagnostics and treatments—are included in this table primarily for the convenience of SMEs and knowledge engineers. That is, for some diseases it is useful to create a snapshot of all relevant aspects of disease even if not all necessary information can be confined to the cells of the table. In effect, what is listed in the table about diagnostics and treatments are methodologically useful pointers to external data sources.

Diagnostics. As concerns diagnostic procedures, what is provided by SMEs is:

a) relevant diagnostic tests for a given disease;
b) the inventory of possible results for each test; and c) the physiological property values of the VP that should give rise to each result.

Armed with this information, in some embodiments, the system automatically generates test results for the VP at any time during disease progression. As such, the inventory of test results and expected outcomes recorded in the disease-modeling table is purely for reference by human developers. The knowledge actually used to generate results in simulation is divided among two other resources: the ontology and what is called the Test Results Inventory (TRI).

The ontology contains basic information about all tests, recorded using a few dozen properties-value pairs. (Many of these are central to virtual tutoring.) Among these property values is the inventory of results for the given test. For example, the results of ESOPHAGEAL-MANOMETRY include dilated esophagus, bird's beak, hypertensive LES, incomplete relaxation of LES, etc. We record these test results as strings, not ontological concepts, because we consider their status to be similar to that of lexical items in natural language processing (NLP). They are not, themselves, ontological but their semantics should be grounded in the ontological metalanguage. This ontological connection is realized by mapping the test results to an ontological concept and by describing salient features using ontologically defined properties.

In the TRI, all test results are headed by a human-readable headword, like hypertensive-LES, and are mapped to the concept TEST-RESULT-AS-ENTITY. Their inventory of properties includes:

SPECIALISTS-INTERPRETATION, filled by actual text strings that are returned for the given test; e.g., "bird's beak";

TEST-RESULT-OF, which links the test result to the ontologically defined test;

CONTENT-OF-TEST-RESULT, which contains an ontologically grounded description of the properties of the VP that generate this test result; e.g., the test result "bird's beak" is returned only if, at the time of the test, the lower body of the esophagus of the VP is greater than 5 cm. in diameter and his/her LES during swallowing is less than 0.5 cm.

During simulation, in some embodiments, whenever a trainee orders a diagnostic procedure, the simulator scans the inventory of test results for that procedure to determine for which the VP has the requisite property values. The simulator returns one of the text strings (there may be many paraphrases) listed in the field SPECIALISTS-OPINION for each applicable result. In some embodiments, the test results are not stored as strings, but are generated on the fly using the natural language processing generator. It is in this way that test results automatically derive from the physiology of the VP. To emphasize the dependencies still further, it is noted that a disease does not directly create given test results at a given time; instead, the disease changes a VP's property values and that change is visible when a diagnostic procedure is launched at a given time. Therefore, while it is useful for SMEs and knowledge engineers to use the disease table as a crib for keeping track of diagnostics and their expected results, any diagnostics-based information recorded there is ignored by the simulator that is interested only in the property values that define the VP at a given time. In some embodiments, the selection of visible human data and procedure results is made at a more atomic level, e.g., there are 5 separate test elements from a virtual patient that produce a single diagnostic test result, and the results for the five elements are reported separately.

Treatments. The final block of the disease table, treatments, also primarily supports knowledge elicitation rather than processing. Here the reason is purely practical—there is no convenient way to view tables that are big enough to incorporate all of the necessary knowledge. That is, each treatment scenario is actually its own table (e.g., script) with its own timeline, physiological effects, symptoms, and other properties. Moreover, there can be many different treatment and outcome scenarios for different patients with different profiles. Nevertheless, there are two good reasons to include treatments in the disease table metaphor anyway, in some embodiments:

1) the utility of creating a snapshot view of a disease to guide knowledge elicitation is desirable; and 2) in many cases, upon exiting a treatment scenario, the VP returns to some point in the original disease table—albeit with the timeline shifted accordingly.

Therefore, when it comes to treatments, the notion of being popped out of the original disease table for treatment, then being popped back in (usually to a different stage of the disease) if the treatment was anything but definitive is extremely useful.

5.3 Authoring Example

It is very straightforward to author an instance of a VP with these embodiments. It amounts to selecting one of the listed options at each choice point delineated for the given disease—which, as broadly understood, includes associated symptoms and treatments as well. Note that a VP author need not select a value for every single property of the VP (eye color, height, weight, BMI, etc.), although this may be done. The author only selects values for those properties explicitly called for in the model of the disease from which the VP suffers. Supplying the patient with a name and a gender supports natural language interaction. In some embodiments, the author is given an option to explicitly select any other property values of the VP as well, giving authors maximum control over the features of a virtual patient Consider an example template filled out to create an achalasia patient:

name;

gender;

basic LES pressure (from Table 1, t0);

values for t1, t2, t3, t4;

values for all symptoms at the start of all t-values (that is, 5 values, with calculation of intermediate values carried out by the simulator);

scenarios for each type of treatment if administered at each stage of the disease (this is actually a series of choices, including VP property values during treatment and the disease state after treatment); and the time at which the VP first sees the physician.

Filling out such a template for a VP is very quick because so much is already recorded about the eventualities of VPs with the disease. The extensive work on knowledge elicitation, formulation and implementation effectively turns a massive essay exam (what happens to a patient with disease X?) into a simple multiple-choice test.

6. Computer System Overview

Figure 4:
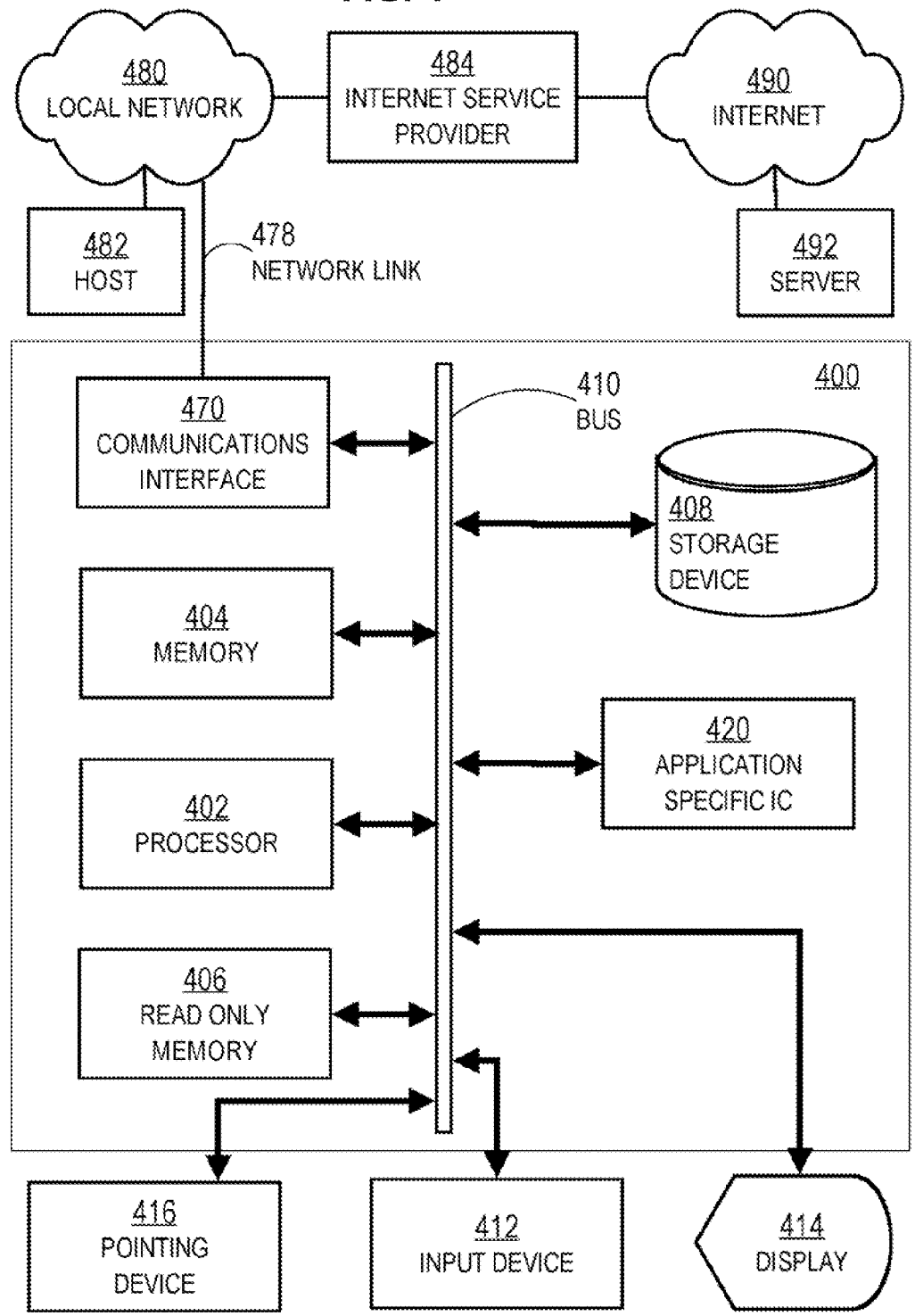
FIG. 4 is a block diagram that illustrates a computer system upon which an embodiment of the invention may be implemented.

FIG. 4 is a block diagram that illustrates a computer system 400 upon which an embodiment of the invention may be implemented. Computer system 400 includes a communication mechanism such as a bus 410 for passing information between other internal and external components of the computer system 400. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 410 includes many parallel conductors of information so that information is transferred quickly among devices coupled to the bus 410. One or more processors 402 for processing information are coupled with the bus 410. A processor 402 performs a set of operations on information. The set of operations include bringing information in from the bus 410 and placing information on the bus 410. The set of operations also typically include comparing two or more units of information, shifting positions of units of information, and combining two or more units of information, such as by addition or multiplication. A sequence of operations to be executed by the processor 402 constitute computer instructions.

Computer system 400 also includes a memory 404 coupled to bus 410. The memory 404, such as a random access memory (RAM) or other dynamic storage device, stores information including computer instructions. Dynamic memory allows information stored therein to be changed by the computer system 400. RAM allows a unit of information stored at a location called a memory address to be stored and retrieved independently of information at neighboring addresses. The memory 404 is also used by the processor 402 to store temporary values during execution of computer instructions. The computer system 400 also includes a read only memory (ROM) 406 or other static storage device coupled to the bus 410 for storing static information, including instructions, that is not changed by the computer system 400. Also coupled to bus 410 is a non-volatile (persistent) storage device 408, such as a magnetic disk or optical disk, for storing information, including instructions, that persists even when the computer system 400 is turned off or otherwise loses power.

Information, including instructions, is provided to the bus 410 for use by the processor from an external input device 412, such as a keyboard containing alphanumeric keys operated by a human user, or a sensor. A sensor detects conditions in its vicinity and transforms those detections into signals compatible with the signals used to represent information in computer system 400. Other external devices coupled to bus 410, used primarily for interacting with humans, include a display device 414, such as a cathode ray tube (CRT) or a liquid crystal display (LCD), for presenting images, and a pointing device 416, such as a mouse or a trackball or cursor direction keys, for controlling a position of a small cursor image presented on the display 414 and issuing commands associated with graphical elements presented on the display 414.

In the illustrated embodiment, special purpose hardware, such as an application specific integrated circuit (IC) 420, is coupled to bus 410. The special purpose hardware is configured to perform operations not performed by processor 402 quickly enough for special purposes. Examples of application specific ICs include graphics accelerator cards for generating images for display 414, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 400 also includes one or more instances of a communications interface 470 coupled to bus 410. Communication interface 470 provides a two-way communication coupling to a variety of external devices that operate with their own processors, such as printers, scanners and external disks. In general the coupling is with a network link 478 that is connected to a local network 480 to which a variety of external devices with their own processors are connected. For example, communication interface 470 may be a parallel port or a serial port or a universal serial bus (USB) port on a personal computer. In some embodiments, communications interface 470 is an integrated services digital network (ISDN) card or a digital subscriber line (DSL) card or a telephone modem that provides an information communication connection to a corresponding type of telephone line. In some embodiments, a communication interface 470 is a cable modem that converts signals on bus 410 into signals for a communication connection over a coaxial cable or into optical signals for a communication connection over a fiber optic cable. As another example, communications interface 470 may be a local area network (LAN) card to provide a data communication connection to a compatible LAN, such as Ethernet. Wireless links may also be implemented. For wireless links, the communications interface 470 sends and receives electrical, acoustic or electromagnetic signals, including infrared and optical signals, that carry information streams, such as digital data. Such signals are examples of carrier waves.

The term computer-readable medium is used herein to refer to any medium that participates in providing instructions to processor 402 for execution. Such a medium may take many forms, including, but not limited to, non-volatile media, volatile media and transmission media. Non-volatile media include, for example, optical or magnetic disks, such as storage device 408. Volatile media include, for example, dynamic memory 404. Transmission media include, for example, coaxial cables, copper wire, fiber optic cables, and waves that travel through space without wires or cables, such as acoustic waves and electromagnetic waves, including radio, optical and infrared waves. Signals that are transmitted over transmission media are herein called carrier waves.

Common forms of computer-readable media include, for example, a floppy disk, a flexible disk, a hard disk, a magnetic tape, or any other magnetic medium, a compact disk ROM (CD-ROM), or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 478 typically provides information communication through one or more networks to other devices that use or process the information. For example, network link 478 may provide a connection through local network 480 to a host computer 482 or to equipment 484 operated by an Internet Service Provider (ISP). ISP equipment 484 in turn provides data communication services through the public, world-wide packet-switching communication network of networks now commonly referred to as the Internet 490. A computer called a server 492 connected to the Internet provides a service in response to information received over the Internet. For example, server 492 provides information representing video data for presentation at display 414.

The invention is related to the use of computer system 400 for implementing the techniques described herein. According to one embodiment of the invention, those techniques are performed by computer system 400 in response to processor 402 executing one or more sequences of one or more instructions contained in memory 404. Such instructions, also called software and program code, may be read into memory 404 from another computer-readable medium such as storage device 408. Execution of the sequences of instructions contained in memory 404 causes processor 402 to perform the method steps described herein. In alternative embodiments, hardware, such as application specific integrated circuit 420, may be used in place of or in combination with software to implement the invention. Thus, embodiments of the invention are not limited to any specific combination of hardware and software.

The signals transmitted over network link 478 and other networks through communications interface 470, which carry information to and from computer system 400, are exemplary forms of carrier waves. Computer system 400 can send and receive information, including program code, through the networks 480, 490 among others, through network link 478 and communications interface 470. In an example using the Internet 490, a server 492 transmits program code for a particular application, requested by a message sent from computer 400, through Internet 490, ISP equipment 484, local network 480 and communications interface 470. The received code may be executed by processor 402 as it is received, or may be stored in storage device 408 or other non-volatile storage for later execution, or both. In this manner, computer system 400 may obtain application program code in the form of a carrier wave.

Various forms of computer readable media may be involved in carrying one or more sequence of instructions or data or both to processor 402 for execution. For example, instructions and data may initially be carried on a magnetic disk of a remote computer such as host 482. The remote computer loads the instructions and data into its dynamic memory and sends the instructions and data over a telephone line using a modem. A modem local to the computer system 400 receives the instructions and data on a telephone line and uses an infra-red transmitter to convert the instructions and data to an infra-red signal, a carrier wave serving as the network link 478. An infrared detector serving as communications interface 470 receives the instructions and data carried in the infrared signal and places information representing the instructions and data onto bus 410. Bus 410 carries the information to memory 404 from which processor 402 retrieves and executes the instructions using some of the data sent with the instructions. The instructions and data received in memory 404 may optionally be stored on storage device 408, either before or after execution by the processor 402.

7. Exstensions and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for delivering medical care by improving decision-making skills of medical personnel who deliver the care, comprising the steps of:
receiving normal data that indicates normal conditions in a patient;
receiving abnormality data that indicates an abnormal condition, if any, in an patient;
generating, via a computer, an instance of a virtual patient based on the normal data and the abnormality data, wherein the instance of the virtual patient includes
a physiological component that describes a sufficiently comprehensive physical state of a patient having the abnormal condition to simulate clinical measurements of the patient's condition, and
a patient cognitive component that describes a patient's awareness of symptoms, history of behavior and ability to convey information in response to queries,
wherein both the physiological component and the cognitive component are implemented using a single natural language processor, including representing physical attributes of the physiological component as a hierarchy of ontological concepts;
receiving from a trainee and interpreting action data that indicates a requested action relevant to dealing with the instance of the virtual patient;
generating, via the computer, response data based on the action data and the instance of the virtual patient; and
presenting to the trainee display data based on the response data, wherein the display data indicates information about the instance of the virtual patient available to a medical professional as a result of the requested action,
wherein the hierarchy of ontological concepts includes a Cell-of-Cajal functional class that includes a kit gene functional class, a transmembrane kit protein receptor functional class, an extracellular Epidermal Growth Factor ligand stimulation functional class, a tyrosine kinase biochemistry functional class and a cell growth cycle functional class.

2. A method as recited in claim 1, wherein constructs of the natural language processor include objects, event scripts and engines for advancing event scripts.

3. A method as recited in claim 1, wherein:
the cognitive component includes history data that indicates previous values for a particular object and previous occurrences of a phase in a particular event; and
said step of generating response data further comprises generating a response based on the history data.

4. A method as recited in claim 3, said step of generating response data based on the history data further comprising: reducing the history data to produce reduced history data to simulate forgetfulness; and generating the response data based on the reduced history data.

5. A method as recited in claim 3, wherein:
the cognitive component includes goal data that indicates a goal for the virtual patient and includes plan data that indicates one or more plans for achieving the goal; and
said step of generating response data further comprises determining a next step in a particular plan indicated in the plan data and executing the next step in the particular plan.

6. A method as recited in claim 5, said step of executing the next step in the plan comprising giving one of an incomplete rendering or an untruthful rendering of the history data.

7. A method as recited in claim 5, said step of executing the next step in the plan comprising determining to perform an action contrary to an action indicated by action data input by the trainee.

8. A method as recited in claim 1, wherein:
the cognitive component includes language data that indicates an ability of the virtual patient to understand and express concepts in a particular language; and
said step of generating response data further comprises generating response data based on the language data.

9. A method as recited in claim 8, wherein:
the language data includes a lexicon that associates information about the virtual patient with words in the particular language that the virtual patient uses for that information; and said step of generating response data based on the language data further comprises determining a particular word to express particular information about the virtual patient based on the lexicon.

10. A method as recited in claim 1, wherein:
the method further comprises receiving tutor data that indicates standard practices for treatment of a patient; and
said step of generating response data further comprises generating response data based on the tutor data.

11. A method as recited in claim 10, wherein the tutor data includes a tutor cognitive component that describes a tutor's awareness of prior responses and ability to convey information in response to queries.

12. A non-transitory computer-readable medium carrying one or more sequences of instructions for delivering medical care by improving decision-making skills of medical personnel who deliver the care, wherein execution of the one or more sequences of instructions by one or more processors causes the one or more processors to perform the steps of:
receiving normal data that indicates normal conditions in a patient;
receiving abnormality data that indicates an abnormal condition, if any, in an patient;
generating an instance of a virtual patient based on the normal data and the abnormality data, wherein the instance of the virtual patient includes
a physiological component that describes a sufficiently comprehensive physical state of a patient having the abnormal condition to simulate clinical measurements of the patient's condition, and
a cognitive component that describes a patient's awareness of symptoms, history of behavior and ability to convey information in response to queries,
wherein both the physiological component and the cognitive component are implemented using a single natural language processor, including representing physical attributes of the physiological component as a hierarchy of ontological concepts;
receiving from a trainee and interpreting action data that indicates a requested action relevant to dealing with the instance of the virtual patient;
generating response data based on the action data and the instance of the virtual patient; and
presenting to the trainee display data based on the response data, wherein the display data indicates information about the instance of the virtual patient available to a medical professional as a result of the requested action,
wherein the hierarchy of ontological concepts includes a Cell-of-Cajal functional class that includes a kit gene functional class, a transmembrane kit protein receptor functional class, an extracellular Epidermal Growth Factor ligand stimulation functional class, a tyrosine kinase biochemistry functional class and a cell growth cycle functional class.

13. An apparatus for delivering medical care by improving decision-making skills of medical personnel who deliver the care, comprising:
means for receiving normal data that indicates normal conditions in a patient;
means for receiving abnormality data that indicates an abnormal condition, if any, in an patient;
means for generating an instance of a virtual patient based on the normal data and the abnormality data, wherein the instance of the virtual patient includes
a physiological component that describes a sufficiently comprehensive physical state of a patient having the abnormal condition to simulate clinical measurements of the patient's condition, and
a cognitive component that describes a patient's awareness of symptoms, history of behavior and ability to convey information in response to queries,
wherein both the physiological component and the cognitive component are implemented using a single natural language processor, including representing physical attributes of the physiological component as a hierarchy of ontological concepts;
means for receiving from a trainee and interpreting action data that indicates a requested action relevant to dealing with the instance of the virtual patient;
means for generating response data based on the action data and the instance of the virtual patient; and
means for presenting to the trainee display data based on the response data, wherein the display data indicates information about the instance of the virtual patient available to a medical professional as a result of the requested action,
wherein the hierarchy of ontological concepts includes a Cell-of-Cajal functional class that includes a kit gene functional class, a transmembrane kit protein receptor functional class, an extracellular Epidermal Growth Factor ligand stimulation functional class, a tyrosine kinase biochemistry functional class and a cell growth cycle functional class.

14. A method as recited in claim 1, wherein the physiological component describes a sufficiently comprehensive physical state of the patient having the abnormal condition to simulate substantively all clinical measurements of the patient's condition.

15. A method as recited in claim 1, wherein the hierarchy of ontological concepts includes a liver class that defines a liver in the virtual patient, and the liver class includes a hepatocyte class that defines a number of cells that function as a hepatocyte unit within a liver and includes a Kupffer class that defines a different number of cells within the liver.

16. A method as recited in claim 1, wherein the hierarchy of ontological concepts includes at least one of an event script configured to represent nausea or an event script configured to represent swallowing.

17. A method as recited in claim 1, wherein each of the patient cognitive component and the physiological component includes a long term memory, a short term memory, a perception process, a reasoning process and an execution process.

18. A method as recited in claim 1, wherein a disease script uses a object-oriented table that describes a first timeline of physiological properties and values and a second timeline of symptoms.

19. A method as recited in claim 18, wherein the object-oriented table also describes at least one of a third timeline of results of diagnostic tests or a fourth timeline of effective treatments.

* * * * *